(12) United States Patent
Kobayashi et al.

(10) Patent No.: US 11,443,544 B2
(45) Date of Patent: Sep. 13, 2022

(54) ELECTRONIC DEVICE

(71) Applicant: SONY CORPORATION, Tokyo (JP)

(72) Inventors: Naoko Kobayashi, Tokyo (JP);
Yasunori Kamada, Kanagawa (JP);
Hiroyuki Shigei, Tokyo (JP); Toru Amano, Tokyo (JP); Futoshi Takeuchi, Tokyo (JP); Toshio Enokido, Kanagawa (JP); Yusuke Sato, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/971,429

(22) PCT Filed: Dec. 28, 2018

(86) PCT No.: PCT/JP2018/048529
§ 371 (c)(1),
(2) Date: Aug. 20, 2020

(87) PCT Pub. No.: WO2019/167425
PCT Pub. Date: Sep. 6, 2019

(65) Prior Publication Data
US 2021/0004554 A1 Jan. 7, 2021

(30) Foreign Application Priority Data
Feb. 27, 2018 (JP) .............................. JP2018-033776

(51) Int. Cl.
*G06V 40/13* (2022.01)
*G06F 3/044* (2006.01)
*F21V 8/00* (2006.01)
*G06F 3/041* (2006.01)

(52) U.S. Cl.
CPC .......... *G06V 40/1306* (2022.01); *G02B 6/003* (2013.01); *G06F 3/0412* (2013.01); *G06F 3/0446* (2019.05)

(58) Field of Classification Search
None
See application file for complete search history.

(56) References Cited

U.S. PATENT DOCUMENTS

| | | | |
|---|---|---|---|
| 2010/0026453 A1 | 2/2010 | Yamamoto | |
| 2015/0186705 A1* | 7/2015 | Magi | G06F 1/163 |
| | | | 382/125 |
| 2017/0097702 A1* | 4/2017 | Chang | H04N 1/10 |
| 2017/0153128 A1 | 6/2017 | Rudmann et al. | |
| 2017/0220844 A1* | 8/2017 | Jones | A61B 5/1172 |

(Continued)

FOREIGN PATENT DOCUMENTS

| | | |
|---|---|---|
| CN | 107526953 A | 12/2017 |
| CN | 209982564 U | 1/2020 |

(Continued)

*Primary Examiner* — Nicholas J Lee
(74) *Attorney, Agent, or Firm* — Paratus Law Group, PLLC

(57) ABSTRACT

An electronic device including: a transparent panel section in which a plurality of transparent light-emitting elements is disposed; and an imaging section that is disposed under a partial region of the transparent panel section, and images, via the transparent panel section, an object which is in contact with or in proximity to the partial region of the transparent panel section.

18 Claims, 21 Drawing Sheets

(56) References Cited

U.S. PATENT DOCUMENTS

| | | | |
|---|---|---|---|
| 2017/0344148 A1* | 11/2017 | Han | G06F 3/04886 |
| 2017/0364763 A1* | 12/2017 | Jin | G06F 21/32 |
| 2018/0039815 A1* | 2/2018 | Jung | G06K 9/0002 |
| 2018/0321780 A1* | 11/2018 | Park | G06F 3/041 |
| 2019/0125221 A1* | 5/2019 | Kobayashi | G06K 9/0004 |
| 2019/0213380 A1* | 7/2019 | Joo | H01L 27/3234 |
| 2020/0142534 A1* | 5/2020 | Gu | G09G 3/3233 |

FOREIGN PATENT DOCUMENTS

| | | |
|---|---|---|
| JP | H06-325158 A | 11/1994 |
| JP | 2001-257835 A | 9/2001 |
| JP | 2006-091462 A | 4/2006 |
| JP | 2012-037575 A | 2/2012 |
| JP | 2017-196319 A | 11/2017 |
| WO | WO-2014115682 A1 | 7/2014 |
| WO | WO 2017/211152 A1 | 12/2017 |

* cited by examiner

[ FIG. 1 ]
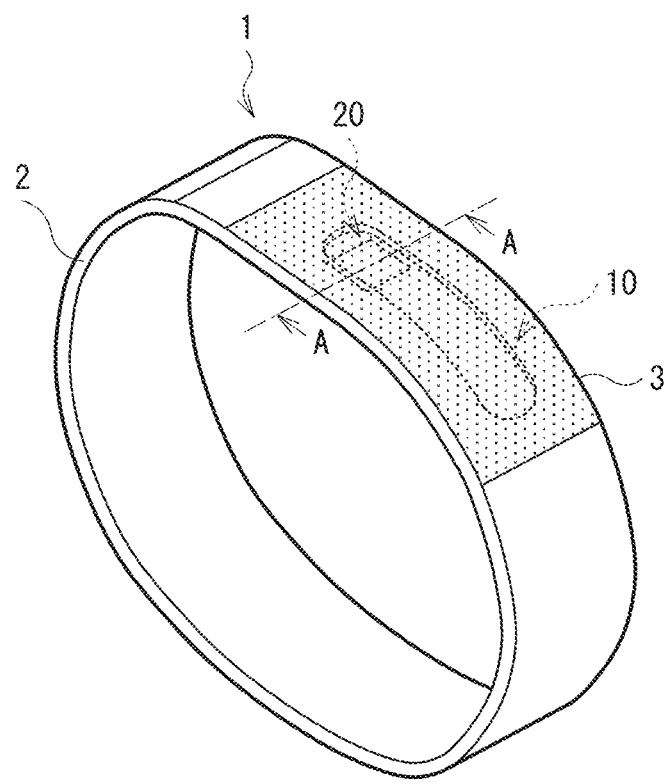
[ FIG. 2 ]
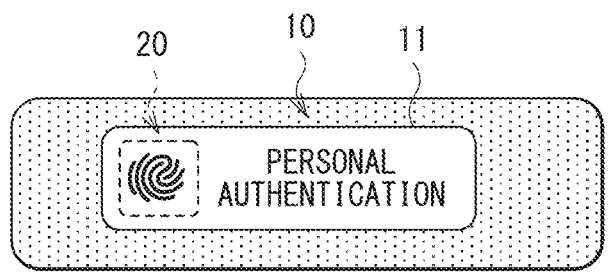

[FIG. 3]
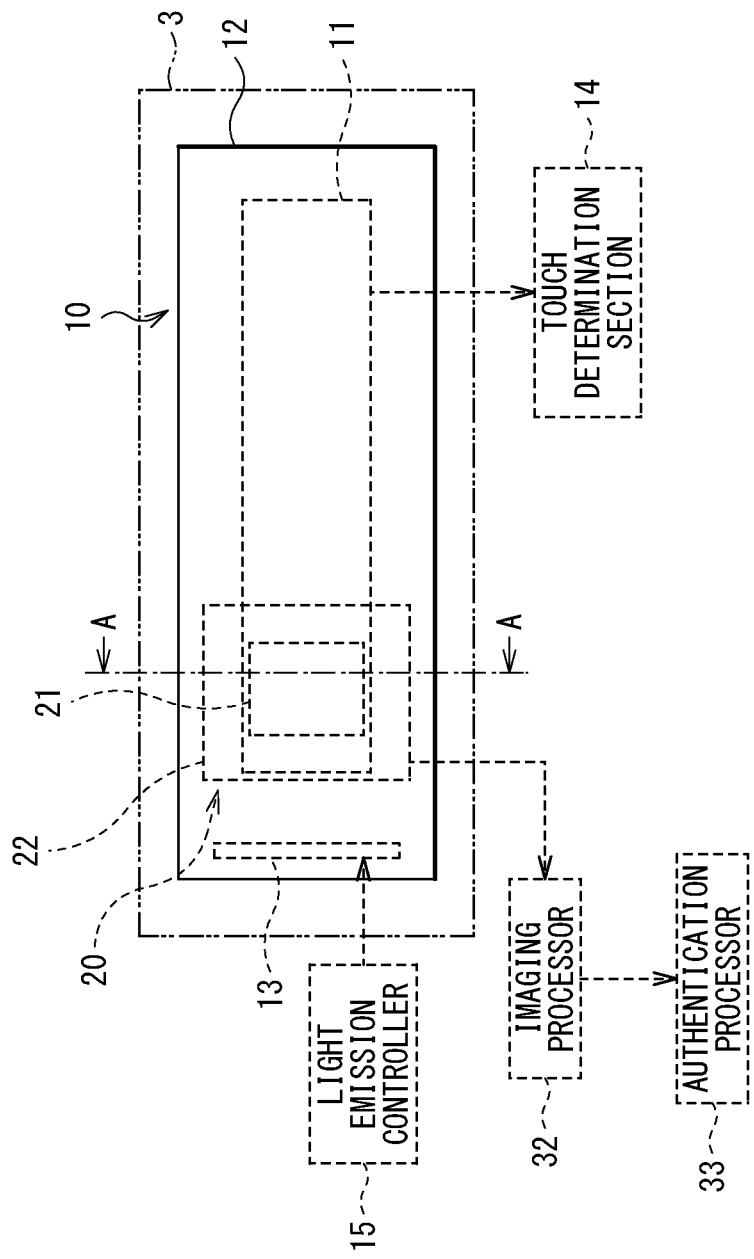

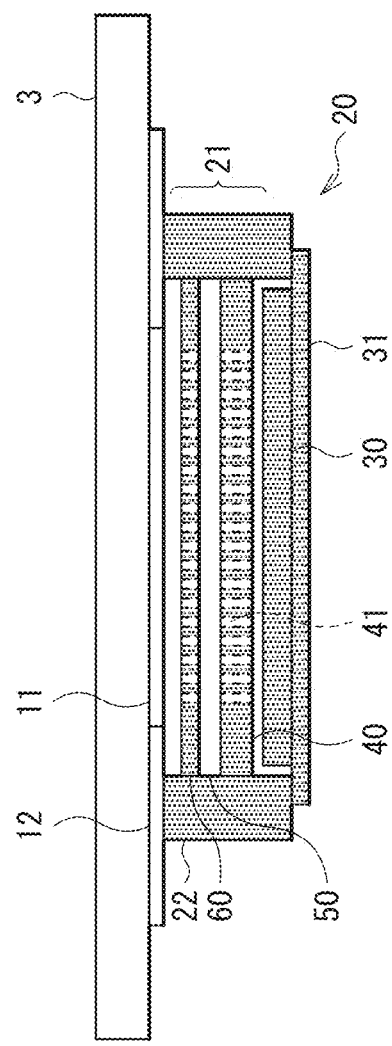
[FIG. 4]

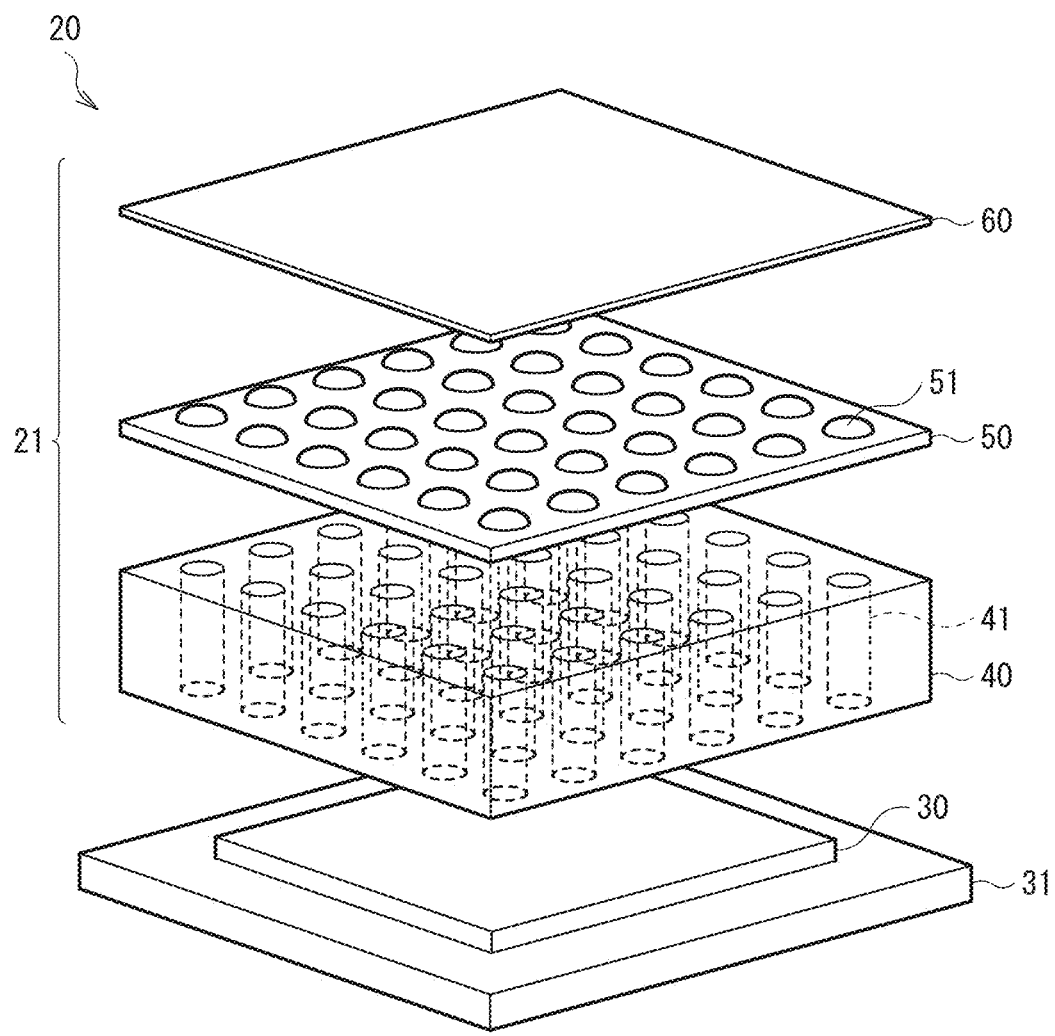
[FIG.5]

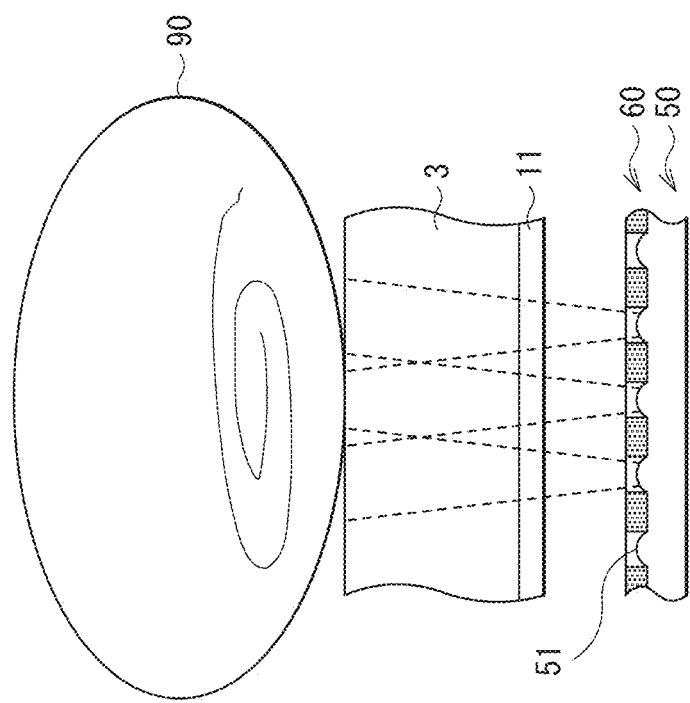
[ FIG. 6 ]

[ FIG. 7 ]
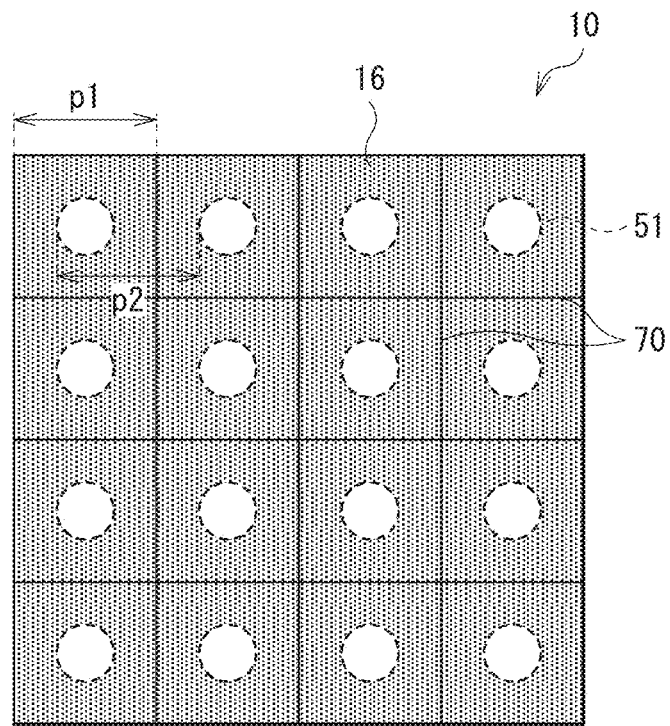
[ FIG. 8 ]
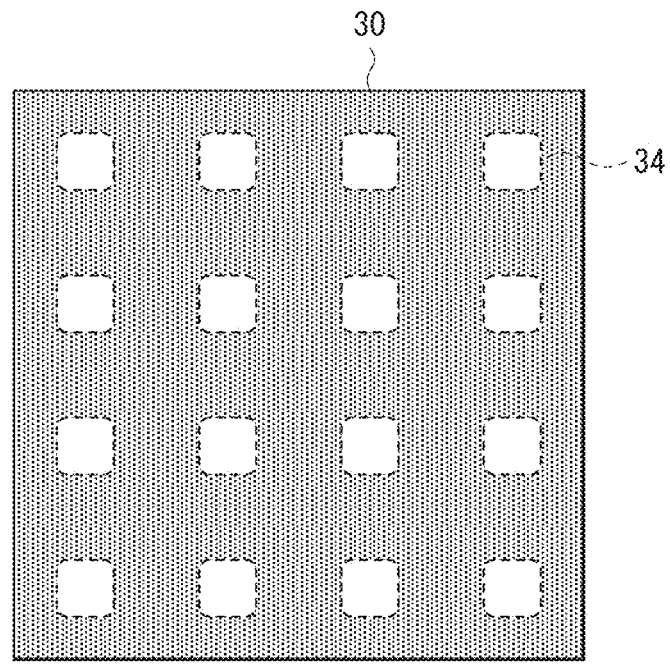

[ FIG. 9 ]
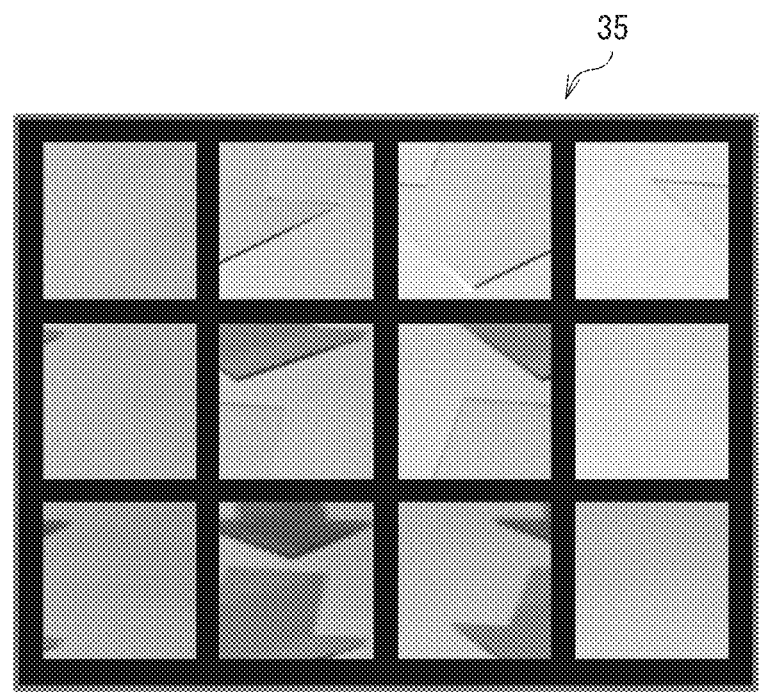
AFTER COMPOSITING
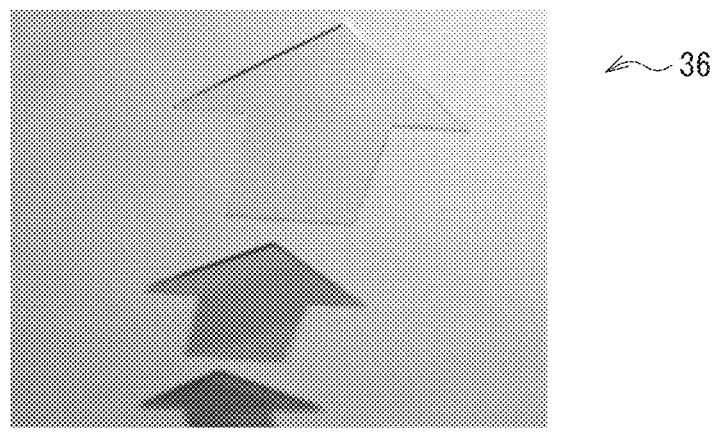

[ FIG. 10 ]
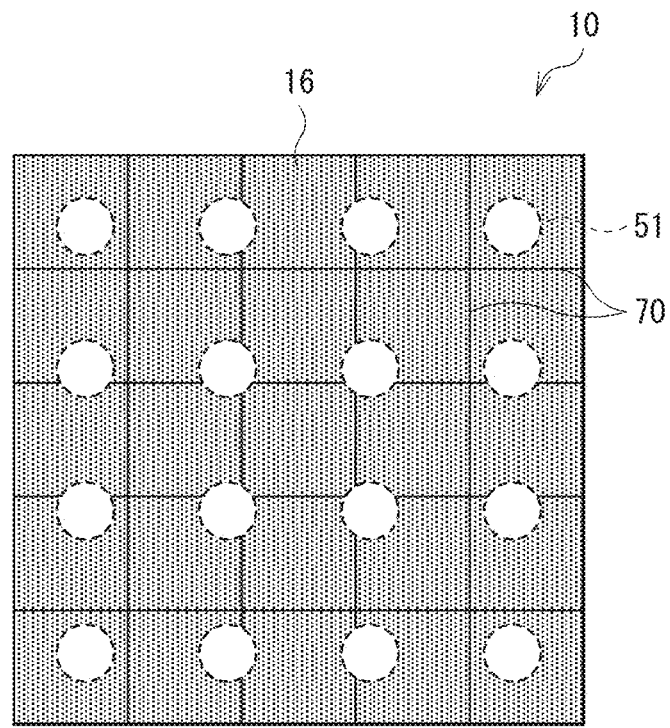
[ FIG. 11 ]
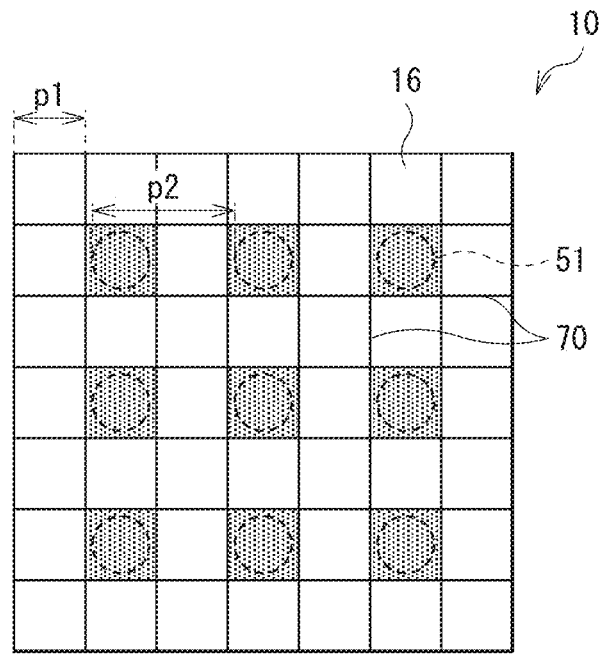

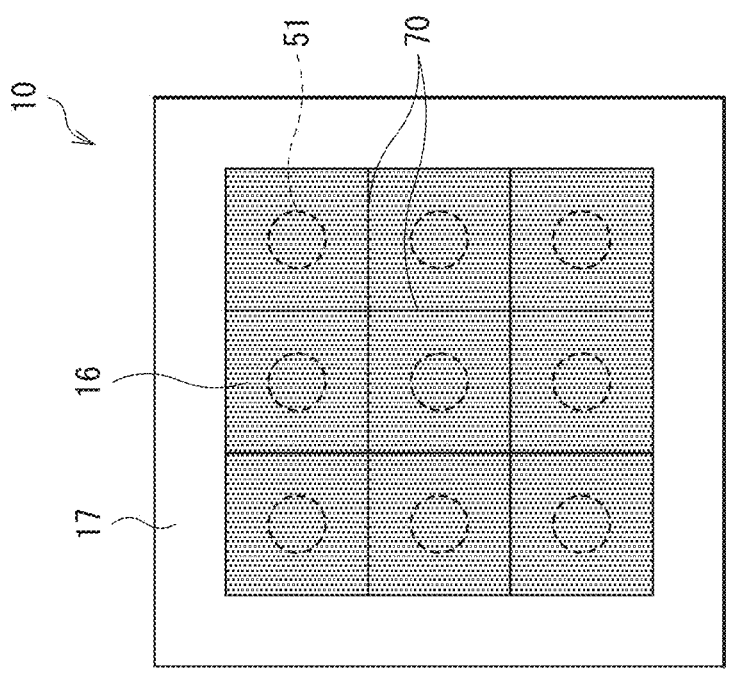
[FIG. 12]

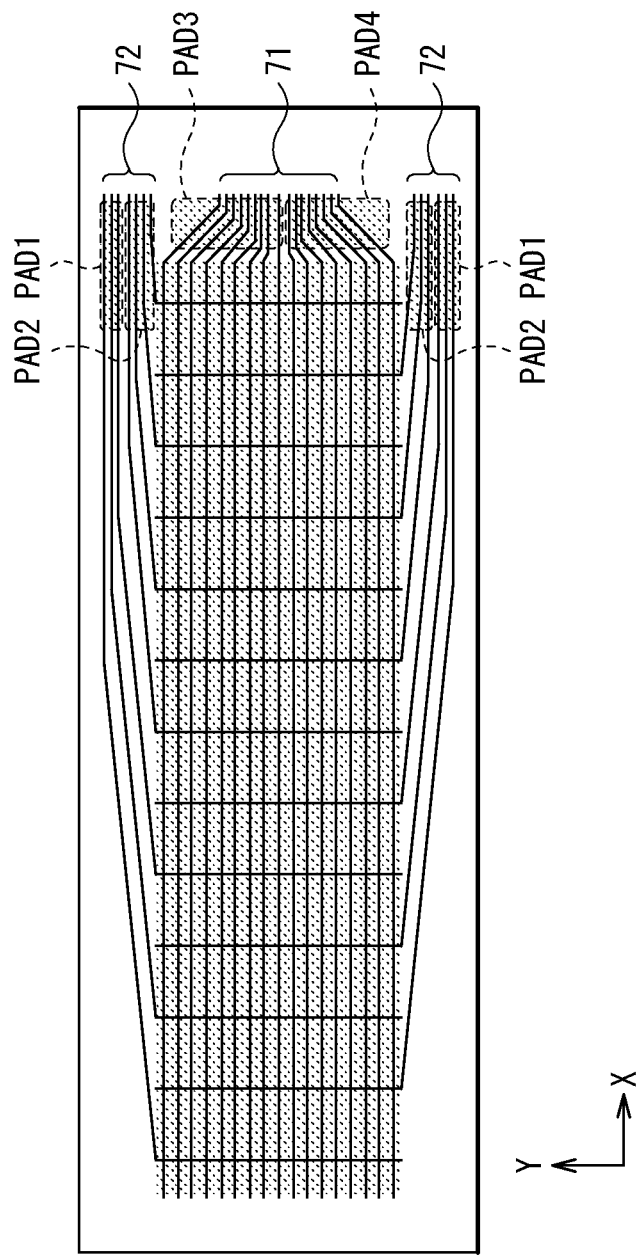

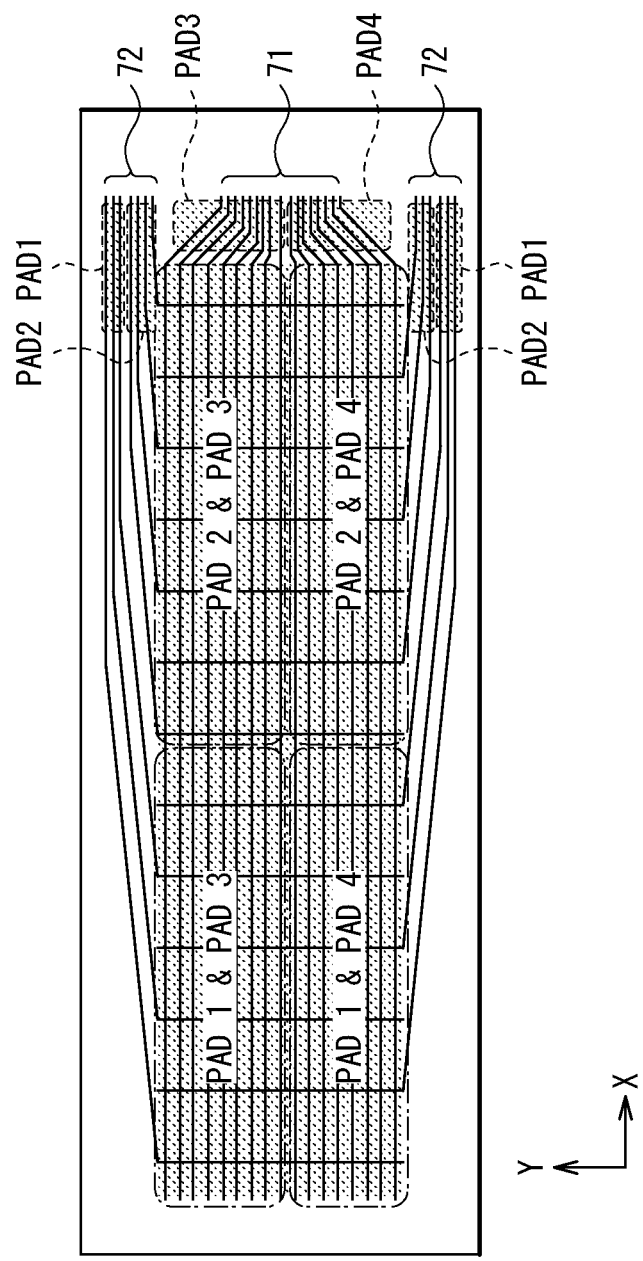

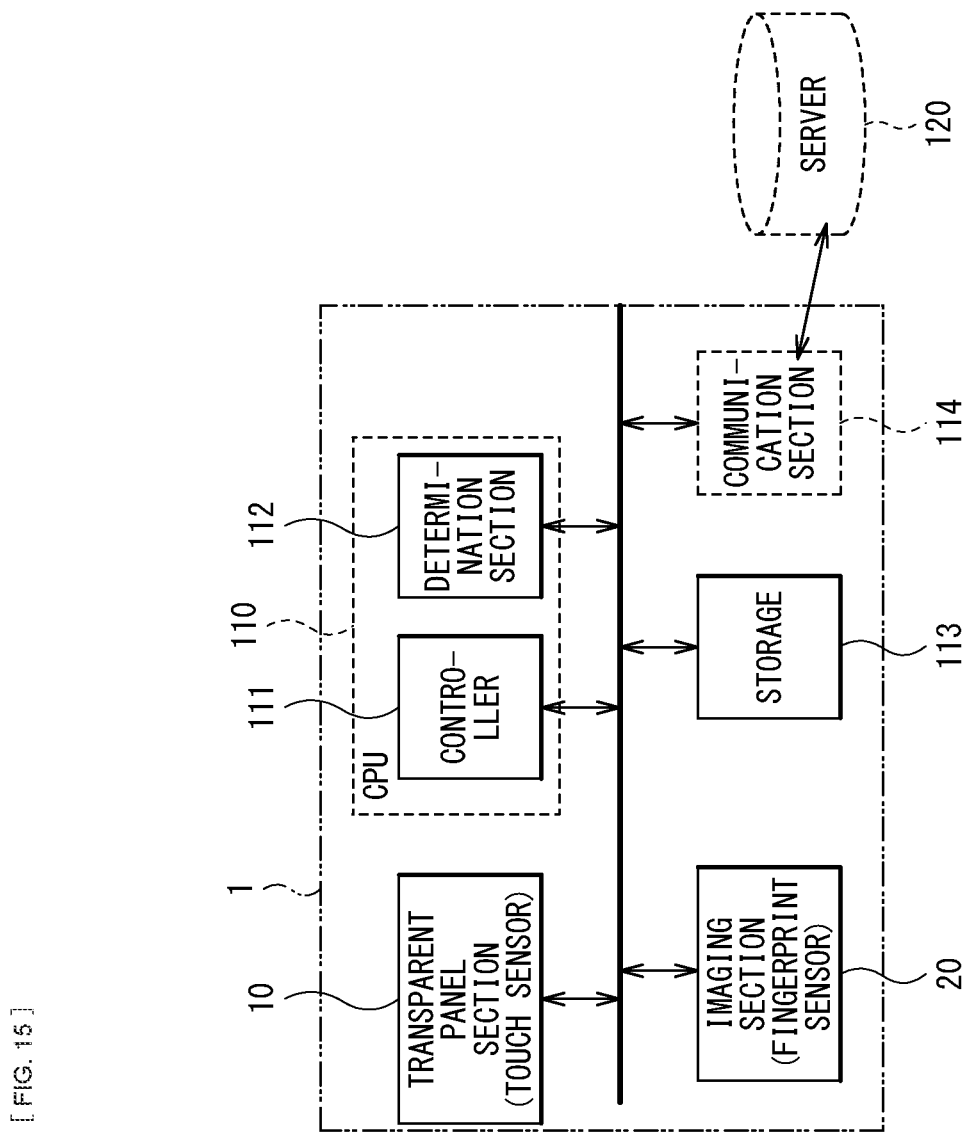
[FIG. 15]

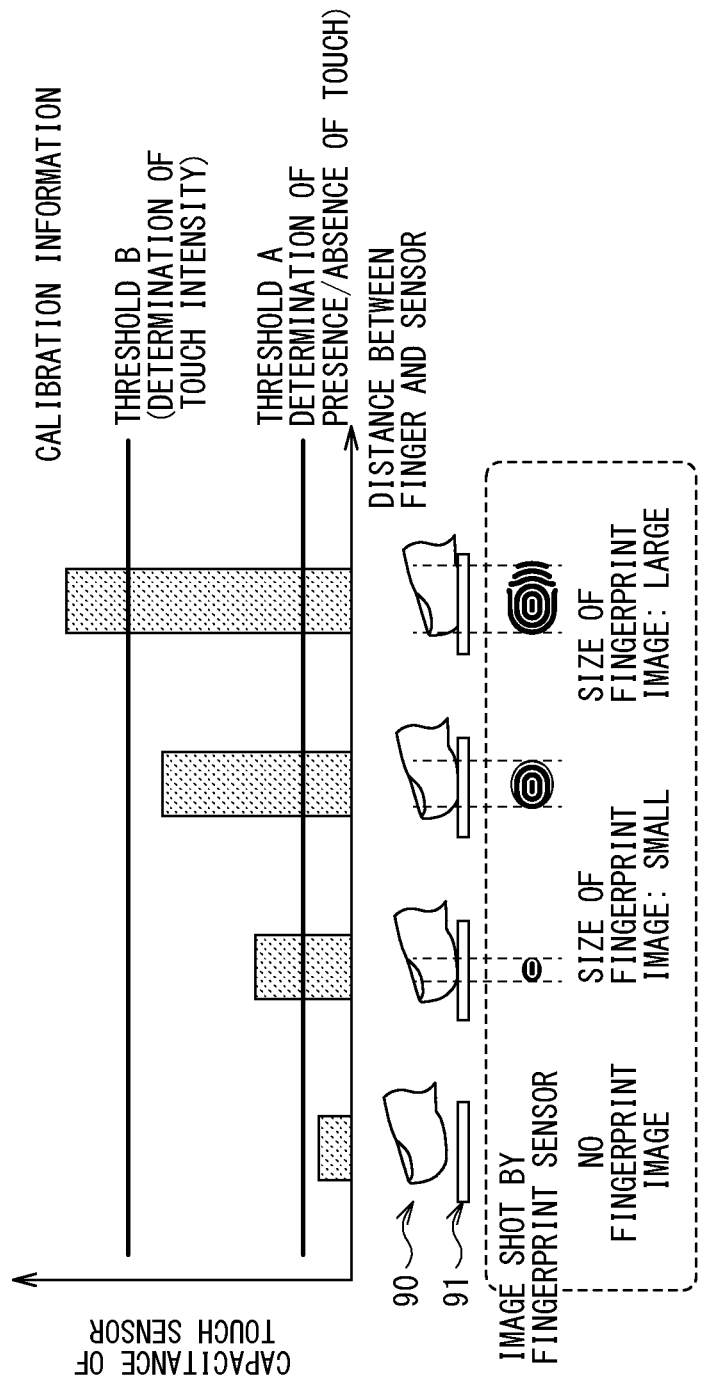
[FIG. 16]

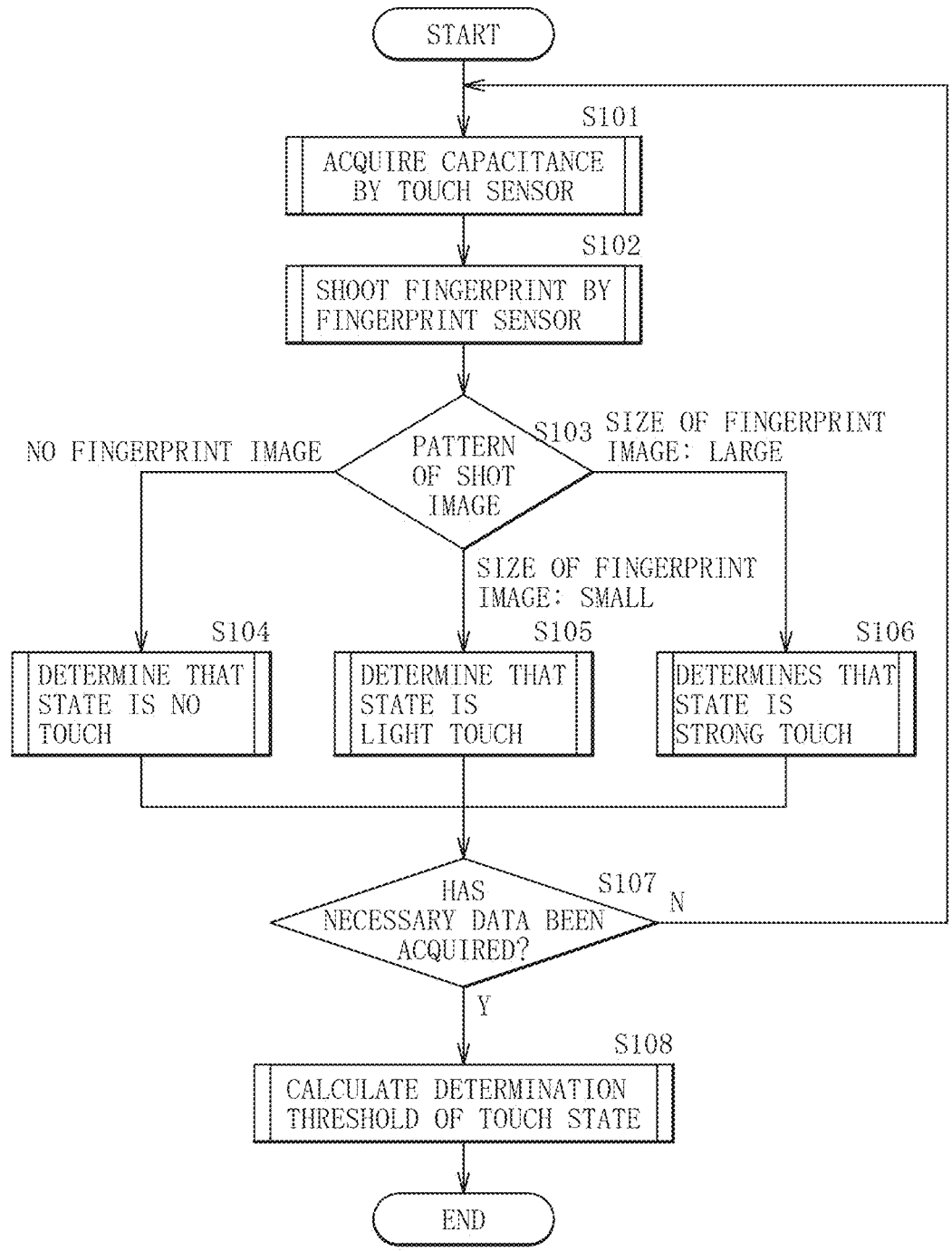

[ FIG. 18 ]
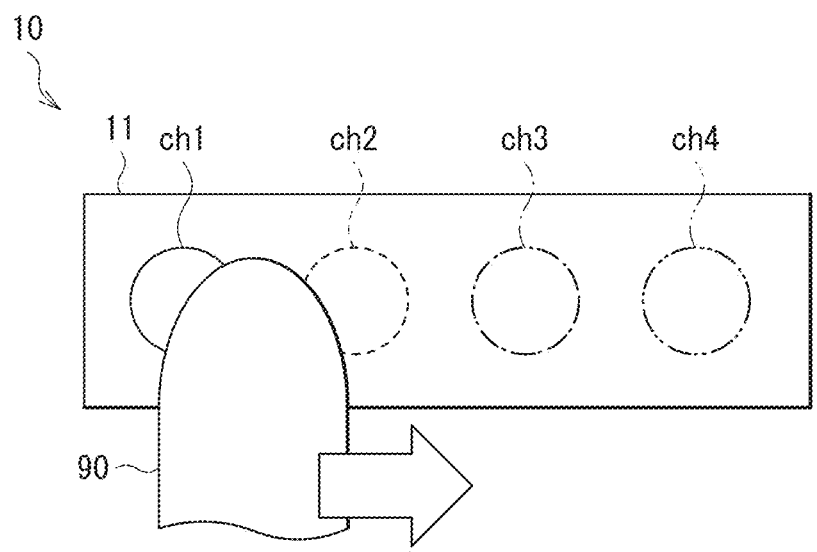
[ FIG. 19 ]
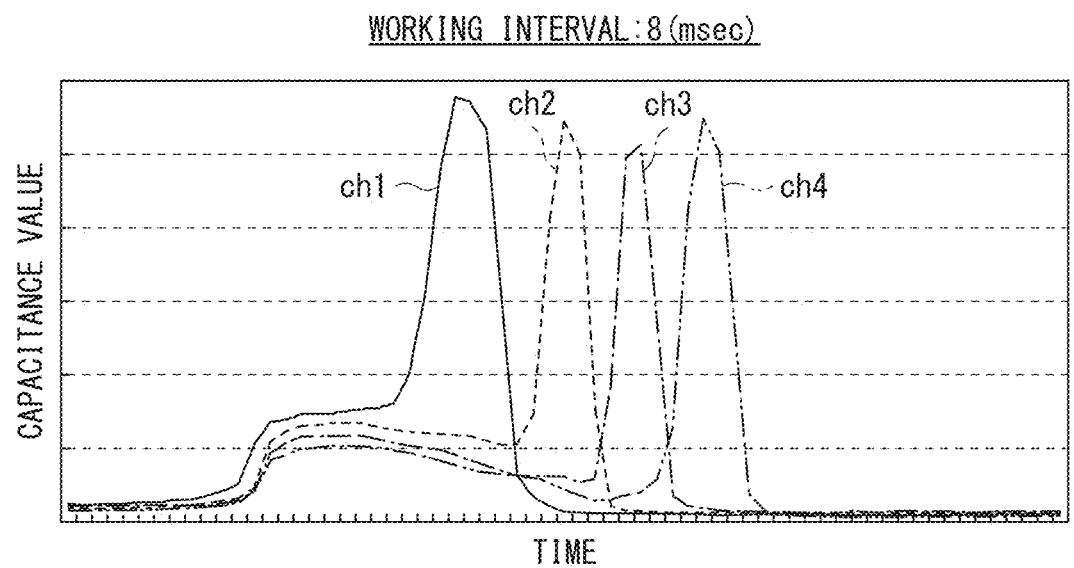

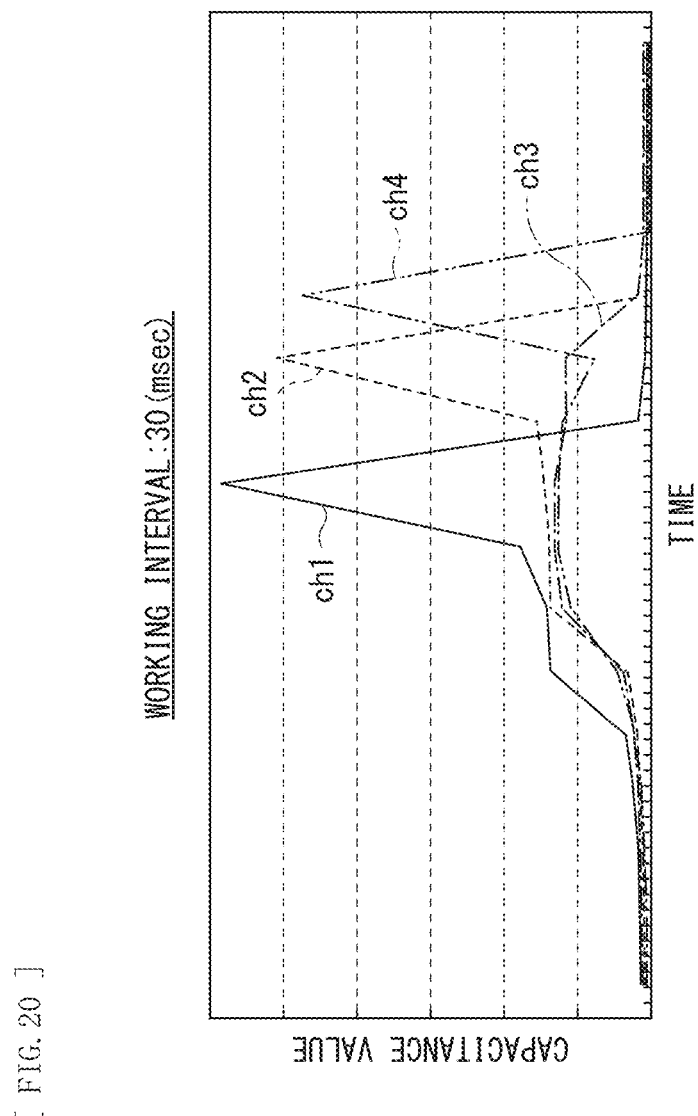
[ FIG. 20 ]

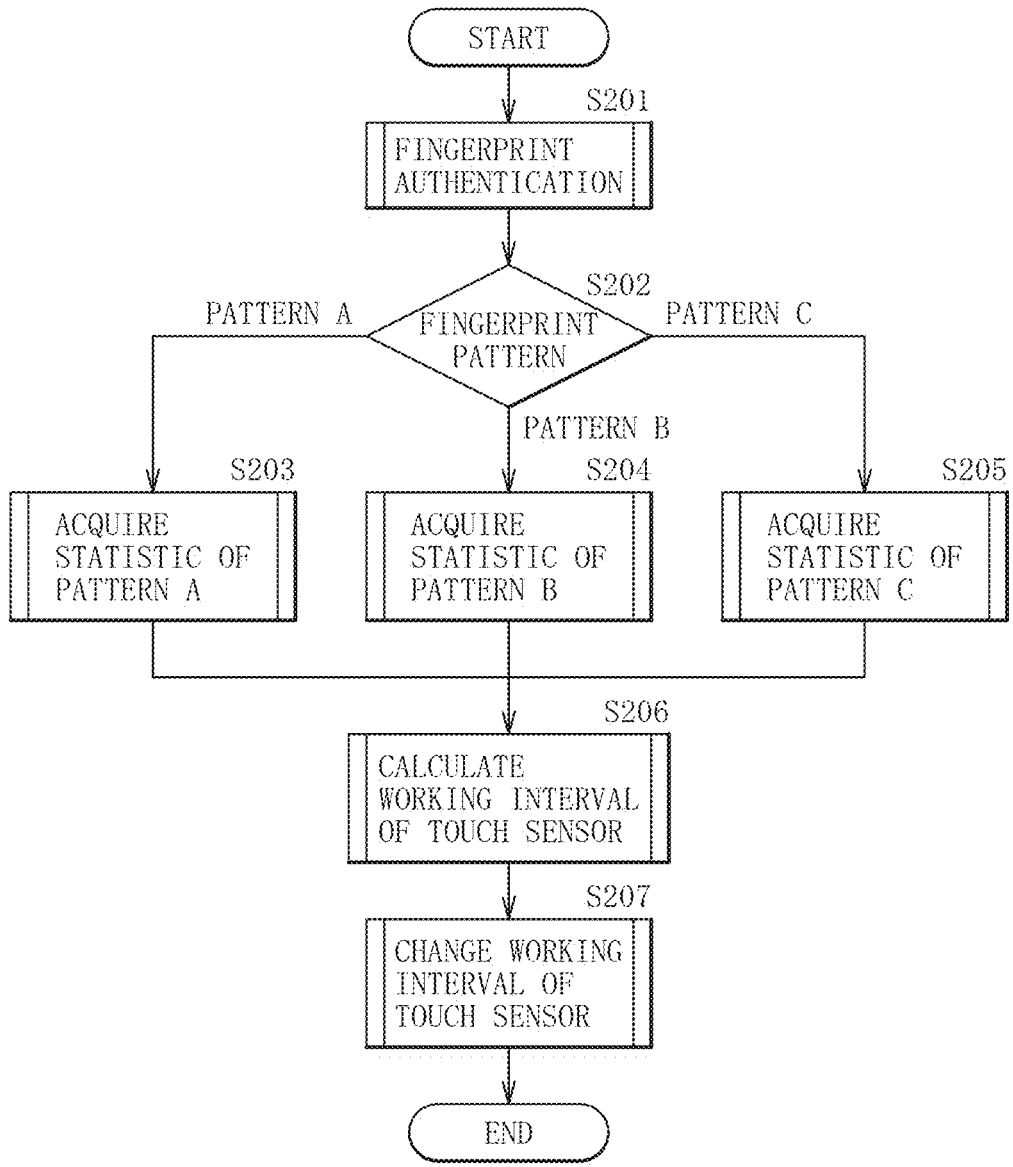
[ FIG. 21 ]

[ FIG. 22 ]

| FINGERPRINT PATTERN (USER) | OPERATION SPEED ||
|---|---|---|
| | SLIDING SPEED (STATISTIC) | TOUCHING SPEED (STATISTIC) |
| A | 10 | 10 |
| B | 3 | 1 |
| C | 5 | 8 |

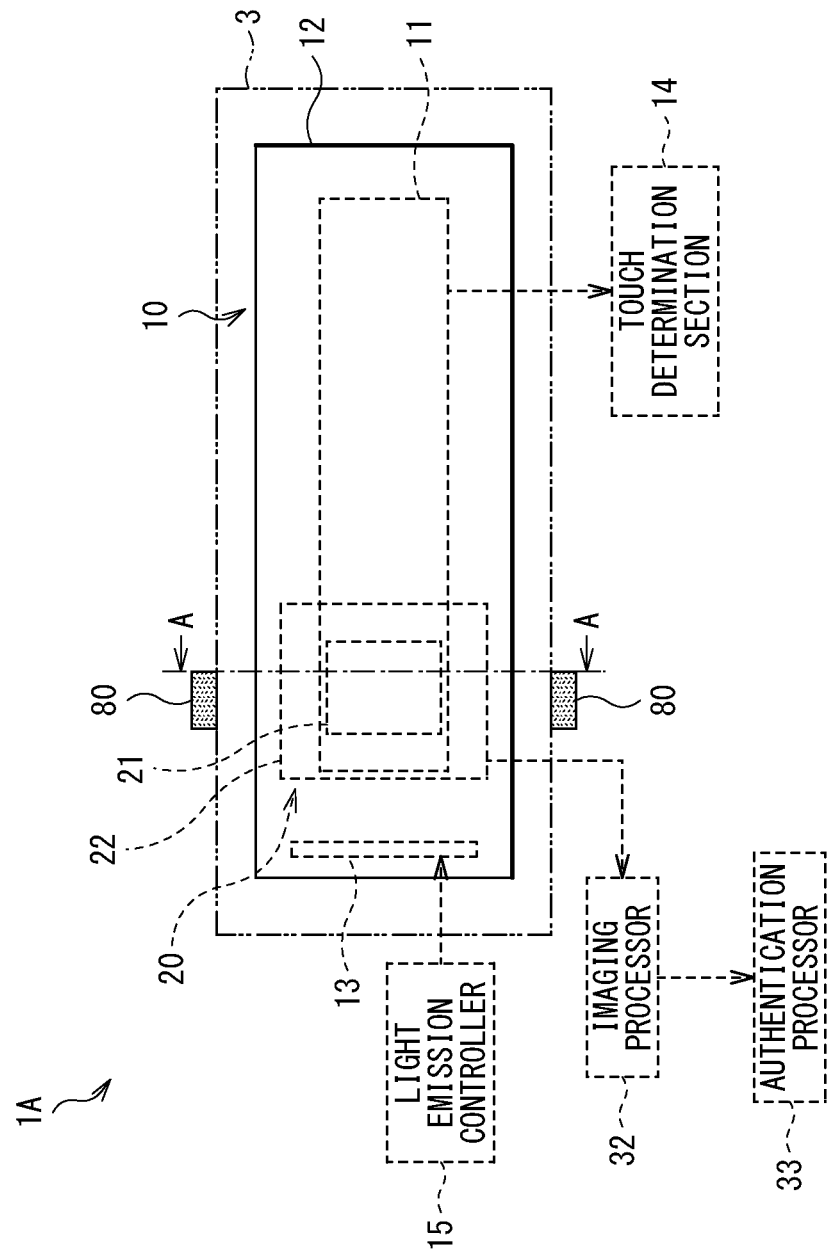

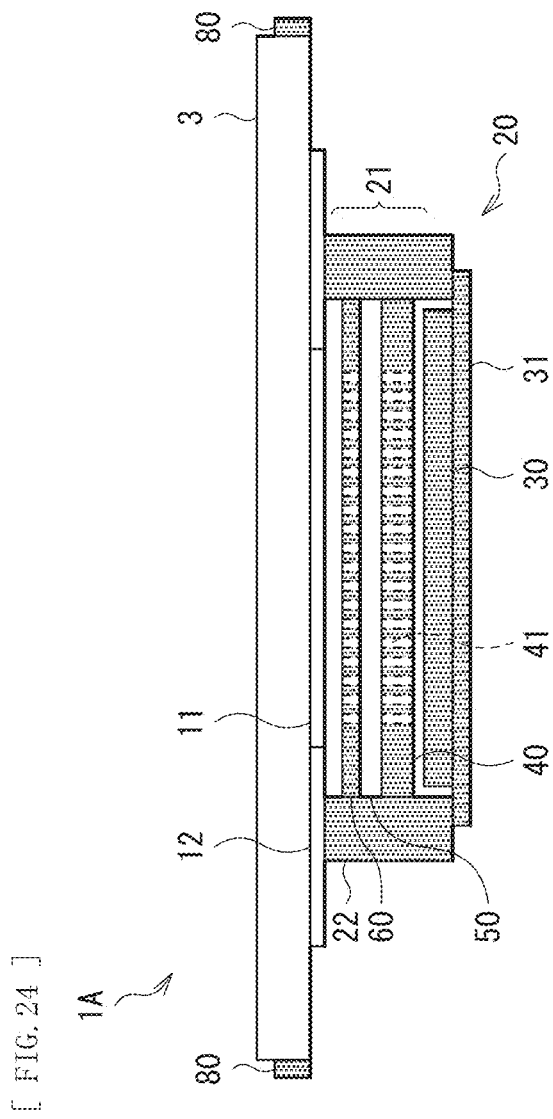
[FIG. 24]

ELECTRONIC DEVICE

TECHNICAL FIELD

The present disclosure relates to an electronic device having an imaging function.

BACKGROUND ART

A device for performing individual authentication using biological information, which is information unique to a living body, has been developed (see PTL 1). Example of a device that performs biometric authentication includes a fingerprint sensor device that performs fingerprint authentication by imaging a surface of a finger. In contrast, a wristband-type small electronic device, for example, has recently been developed.

CITATION LIST

Patent Literature

PTL 1: Japanese Unexamined Patent Application Publication No. 2017-196319

SUMMARY OF THE INVENTION

It is desirable to implement, in a small electronic device, a plurality of functions such as a displaying function and an imaging function, but in some cases, it is difficult to implement desired functions due to a limited surface area. Further, in a case where a fingerprint authentication function is to be implemented, it may be difficult, in a small electronic device, for a fingerprint sensor device to bring a finger to an optimal position.

It is desirable to provide an electronic device that is able to achieve a plurality of functions in a compact size.

An electronic device according to an embodiment of the present disclosure includes a transparent panel section in which a plurality of transparent light-emitting elements is disposed, and an imaging section that is disposed under a partial region of the transparent panel section, and images, via the transparent panel section, an object which is in contact with or in proximity to the partial region of the transparent panel section.

In the electronic device according to an embodiment of the present disclosure, the object which is in contact with or in proximity to the partial region of the transparent panel section is imaged by the imaging section disposed under the partial region of the transparent panel section.

BRIEF DESCRIPTION OF DRAWINGS

FIG. 1 is a schematic external view of a configuration example of an electronic device according to a first embodiment of the present disclosure.

FIG. 2 is an explanatory diagram illustrating a display example of a transparent panel section included in the electronic device according to the first embodiment.

FIG. 3 is a configuration diagram illustrating a main structure of the electronic device according to the first embodiment.

FIG. 4 is a cross-sectional view of the main structure of the electronic device according to the first embodiment.

FIG. 5 is an exploded perspective view of a detailed configuration example of an imaging section included in the electronic device according to the first embodiment.

FIG. 6 is a cross-sectional view of an example of regions to be imaged by microlenses included in the electronic device according to the first embodiment.

FIG. 7 is a plan view of an example of a relationship between a structure of the transparent panel section included in the electronic device according to the first embodiment and disposition positions of the microlenses of the transparent panel section.

FIG. 8 is a schematic plan view of object images formed on an imaging element of the imaging section included in the electronic device according to the first embodiment.

FIG. 9 is an explanatory diagram illustrating an example of a captured image obtained by the imaging section included in the electronic device according to the first embodiment and a post-compositing process image based on the captured image.

FIG. 10 is a plan view of a first modification example of a structure of the transparent panel section included in the electronic device according to the first embodiment and disposition positions of the microlenses of the transparent panel section.

FIG. 11 is a plan view of a second modification example of a relationship between a structure of the transparent panel section included in the electronic device according to the first embodiment and disposition positions of the microlenses of the transparent panel section, and of an example of a light emitting state of the transparent panel section at a time of imaging.

FIG. 12 is a plan view of a third modification example of a relationship between a structure of the transparent panel section included in the electronic device according to the first embodiment and disposition positions of the microlenses of the transparent panel section, and of an example of a light emitting state of the transparent panel section at a time of imaging.

FIG. 13 is a plan view of an example of a wiring structure of the transparent panel section included in the electronic device according to the first embodiment.

FIG. 14 is a plan view of an implementation example of a touch sensor function using wiring lines of the transparent panel section included in the electronic device of the first embodiment.

FIG. 15 is a block diagram illustrating a configuration example of a control system of the electronic device of the first embodiment.

FIG. 16 is an explanatory diagram illustrating an outline of determination thresholds of touch states in the electronic device according to the first embodiment.

FIG. 17 is a flowchart illustrating an outline of a process of calculating a determination threshold of a touch state in the electronic device according to the first embodiment.

FIG. 18 is an explanatory diagram illustrating an example of an operation of a user on a touch sensor in the electronic device according to the first embodiment.

FIG. 19 is a characteristic diagram illustrating a first example of change in values of capacitance with time detected by the touch sensor in the electronic device according to the first embodiment.

FIG. 20 is a characteristic diagram illustrating a second example of change in values of capacitance with time detected by the touch sensor in the electronic device according to the first embodiment.

FIG. 21 is a flowchart illustrating an outline of a process of correcting a working interval of the touch sensor in the electronic device according to the first embodiment.

FIG. 22 is an explanatory diagram illustrating an example of a database related to an operation speed of the user in the electronic device according to the first embodiment.

FIG. 23 is a configuration diagram illustrating a main structure of an electronic device according to a second embodiment.

FIG. 24 is a cross-sectional view of the main structure of the electronic device according to the second embodiment.

MODES FOR CARRYING OUT THE INVENTION

Figure 25:
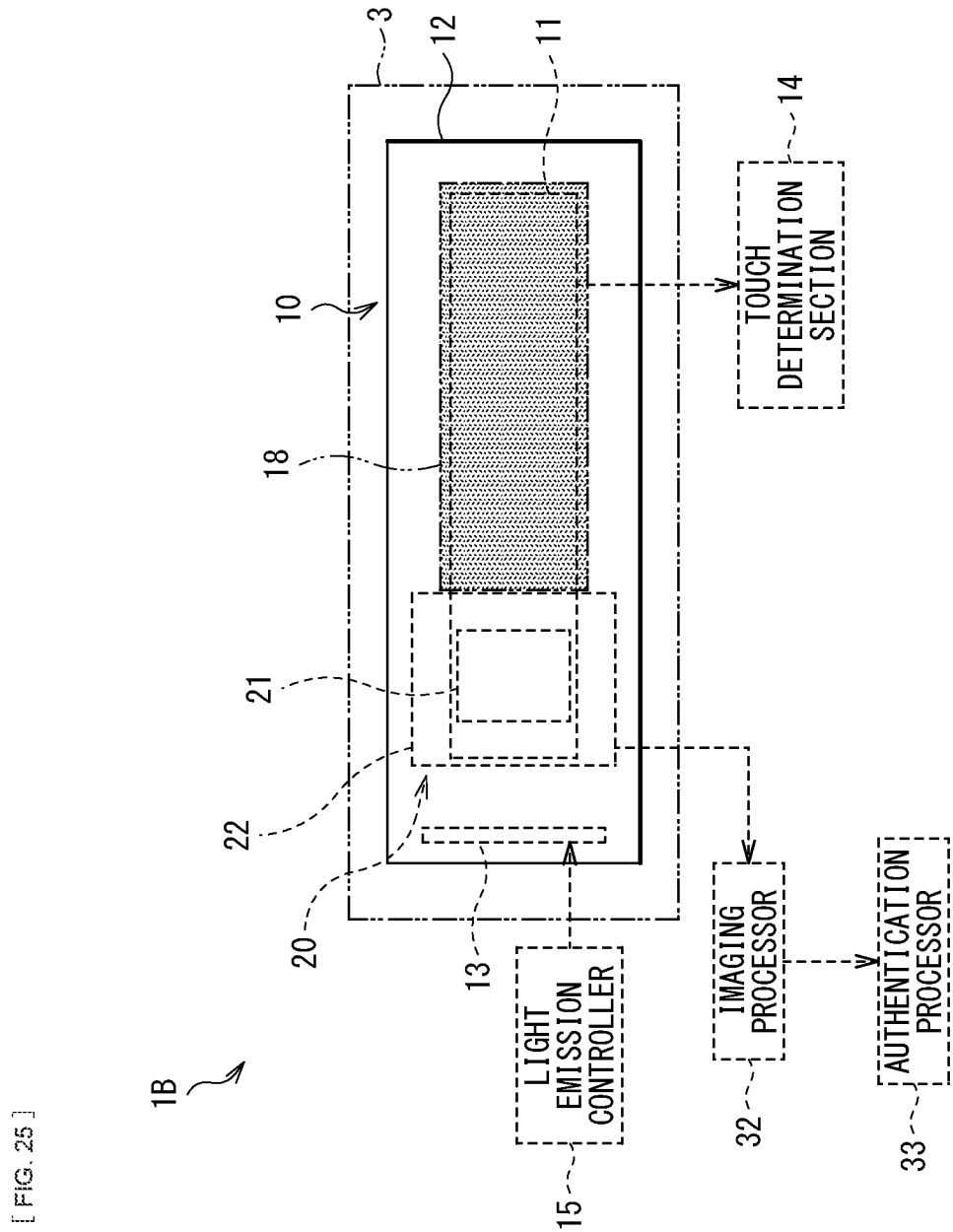
FIG. 25 is a configuration diagram illustrating a main structure of an electronic device according to a third embodiment.

In the following, some embodiments of the present disclosure are described in detail with reference to the drawings. It is to be noted that description is given in the following order.
1. First Embodiment (FIGS. 1 to 22)
　1.1 Outline of Electronic Device
　1.2 Calibration of Touch Sensor
　　1.2.1 Configuration Example of Control System of Electronic Device
　　1.2.2 Calibration of Determination Threshold in Touch State
　　1.2.3 Calibration of Working Interval of Touch Sensor
　1.3 Effects
2. Second Embodiment (FIGS. 23 and 24)
3. Third Embodiment (FIG. 25)
4. Other Embodiments 1. First Embodiment (FIGS. 1 to 22)

[1.1 Outline of Electronic Device]

Although an electronic device according to technology of the present disclosure is applicable to various types of information terminals and the like, an example will be given in which the technology of the present disclosure is applied to a wristband-type electronic device as one example in the present embodiment.

[Overall Configuration of Electronic Device 1]

FIG. 1 schematically illustrates a configuration example of an electronic device 1 according to a first embodiment of the present disclosure.

The electronic device 1 includes a wristband body 2 having a ring shape, a transparent panel section 10 and an imaging section 20 provided on a portion of the wristband body 2, and a cover glass 3 provided on an upper surface of the transparent panel section 10. The cover glass 3 and a panel section-valid region 11 of the transparent panel section 10 may each be transparent as a whole.

The transparent panel section 10 includes a plurality of transparent light-emitting elements 16 arranged in a matrix as illustrated in FIG. 7, which will be described later, a plurality of wiring lines for light-emitting elements coupled to the respective plurality of transparent light-emitting elements 16, and a lattice-shaped structural member 70 that separates the plurality of transparent light-emitting elements 16 from each other. The transparent light-emitting element 16 includes, for example, a transparent organic EL (Electro Luminescence) element (transparent OLED (Organic Light Emitting Diode)). Alternatively, the transparent light-emitting element 16 may also be a quantum dot light-emitting element.

The transparent panel section 10 has a function as a display panel for displaying an image on the panel section-valid region 11 using light emitted by the plurality of transparent light-emitting elements 16. Further, the transparent panel section 10 has a function as a touch sensor for detecting a touch state of an object such as a finger or the like on the basis of a value of capacitance between the plurality of wiring lines for light-emitting elements, for example.

The imaging section 20 is disposed under a partial region of the transparent panel section 10. The imaging section 20 has a function of imaging, via the transparent panel section 10, an object which is in contact with or in proximity to the partial region of the transparent panel section 10. The object to be imaged by the imaging section 20 may be, for example, a portion of a living body. The imaging section 20 may have a function of a biometric authentication device that performs biometric authentication on a part of a living body on the basis of a captured image of the part of the living body obtained by imaging the part of the living body. The function as the biometric authentication device of the imaging section 20 enables a configuration of a fingerprint sensor, for example, FIG. 2 illustrates a display example of the transparent panel section 10 included in the electronic device 1.

The transparent panel section 10 includes, for example, the panel section-valid region 11 that displays various types of information as illustrated in FIG. 2. The various types of information display may be various shapes and various types of text information. For example, as illustrated in FIG. 2, the transparent panel section 10 displays a message indicating performing "personal authentication" in a case where the imaging section 20 is used as a fingerprint sensor, information promoting placing of a finger at a position corresponding to the imaging section 20, and the like.

[Main Structure of Electronic Device 1]

FIGS. 3 and 4 each illustrate a main structure of the electronic device 1. FIG. 3 illustrates a structure of the transparent panel section 10 and a vicinity thereof when the electronic device 1 is viewed from upper side (side of an object to be imaged). FIG. 4 corresponds to a cross-section taken along a line A-A in FIGS. 1 and 3. FIG. 5 illustrates a detailed configuration example of the imaging section 20.

As illustrated in FIGS. 3 and 4, the transparent panel section 10 includes the panel section-valid region 11, a panel section-outer frame 12, and a panel driver 13. The electronic device 1 further includes a touch determination section 14 and a light emission controller 15 coupled to the transparent panel section 10.

In the panel section-valid region 11, as illustrated in FIG. 7 to be described later, a plurality of transparent light-emitting elements 16 is arranged in a matrix.

The touch determination section 14 determines, in a case where the transparent panel section 10 is used as a touch sensor, a state of a touch. The light emission controller 15 controls light emission of the plurality of transparent light-emitting elements 16 via the panel driver 13.

As illustrated in FIGS. 3 and 4, the imaging section 20 includes a microlens array module 21, an imaging section-outer frame 22, an imaging element 30, and a substrate 31. The microlens array module 21 is disposed within the panel section-valid region 11 of the transparent panel section 10 as viewed from the upper side. The electronic device 1 further includes an imaging processor 32 coupled to the imaging element 30 and an authentication processor 33 coupled to the imaging processor 32.

The imaging element 30 includes, for example, a CMOS (Complementary Metal Oxide Semiconductor) sensor. The imaging element 30 is disposed on the substrate 31.

The imaging processor 32 performs predetermined image processing on a captured image obtained by the imaging element 30. The authentication processor 33 performs biometric authentication on the basis of the captured image that has been subjected to the image processing by the imaging processor 32. The authentication processor 33 performs, for example, in a case where the imaging section 20 is used as a fingerprint sensor, a process of fingerprint authentication. The authentication processor 33 authenticates a fingerprint pattern, for example, as the process of the fingerprint authentication. When the fingerprint pattern is to be authenticated, for example, minutiae (ridge ending and bifurcation of a fingerprint) may be used as feature amounts of the fingerprint. Further, the authentication processor 33 may authenticate feature amounts of sweat glands or veins instead of the fingerprint as the biometric authentication. In addition, authentication may be performed by combining two or more feature amounts among the feature amounts of the fingerprint, the sweat glands, and the veins.

As illustrated in FIGS. 4 and 5, the microlens array module 21 is disposed between the imaging element 30 and the panel section-valid region 11 of the transparent panel section 10. The microlens array module 21 includes, in order from the upper side, a cover glass-and-light guide plate 60, a microlens array 50, and a light guide plate 40.

As illustrated in FIG. 5, the microlens array 50 includes a plurality of microlenses 51 arranged in a matrix. The microlens array 50 collects object light from an object such as a finger or the like toward the imaging element 30 by each of the plurality of microlenses 51.

The cover glass-and-light guide plate 60 serves to protect a surface of the microlens array 50. The cover glass-and-light guide plate 60 has a function of bringing the object light transmitted through the panel section-valid region 11 of the transparent panel section 10 to each of the plurality of microlenses 51. The cover glass-and-light guide plate 60 has a plurality of light guide paths each provided at corresponding one of positions of the plurality of microlenses 51.

As illustrated in FIGS. 4 and 5, the light guide plate 40 has a plurality of light guide paths 41. The plurality of light guide paths 41 is each provided at corresponding one of the positions of the plurality of microlenses 51, and brings the light collected by each of the plurality of microlenses 51 to the imaging element 30.

FIG. 6 illustrates an example of regions to be imaged by the microlenses 51 of the imaging section 20. FIG. 7 illustrates an example of a relationship between a structure of the transparent panel section 10 and disposition positions of the microlenses 51 of the imaging section 20. FIG. 8 schematically illustrates object images 34 formed on the imaging element 30 of the imaging section 20. FIG. 9 illustrates an example of a captured image 35 by obtained by the imaging section 20 and a post-compositing process image 36 based on the captured image 35.

As illustrated in FIG. 7, the transparent panel section 10 includes the plurality of wiring lines for light-emitting elements coupled to the respective plurality of transparent light-emitting elements 16 arranged in a matrix, and the lattice-shaped structural member 70 that separates the plurality of transparent light-emitting elements 16 from each other. In the imaging section 20, it is preferable that the plurality of microlenses 51 be disposed to cause the plurality of microlenses 51 not to overlap with the lattice-shaped structural member 70 as viewed from the upper side (object side), to cause the lattice-shaped structural member 70 not to be shown in the captured image. The plurality of microlenses 51 may be disposed to cause an arrangement pitch p2 of the plurality of microlenses 51 to be substantially the same as an arrangement pitch p1 of the plurality of transparent light-emitting elements 16.

As illustrated in FIG. 8, a plurality of image portions corresponding to the arrangement pitch p2 of the plurality of microlenses 51 is formed as object images 34 on the imaging element 30 of the imaging section 20. Consequently, as illustrated in FIG. 9, a plurality of partial images is formed as the captured image 35. In the imaging processor 32, as illustrated in FIG. 9, the plurality of partial image in the captured image 35 is subjected to a compositing process to generate the post-compositing process image 36. This generates a whole image of the object.

The imaging section 20 is preferably configured in a manner that imaging regions (light-capturing areas) of adjacent plurality of microlenses 51 with respect to the object (a finger 90) to be imaged are partially overlapped, as illustrated in FIG. 6. Thus, the plurality of partial images whose peripheral portions partially overlap each other is formed as the captured image 35; therefore, in a case where the compositing process is performed as illustrated in FIG. 9, it is possible to generate a seamless whole image without conspicuous seams.

FIG. 10 illustrates a first modification example of a structure of the transparent panel section 10 and disposition positions of the microlenses 51 of the imaging section 20.

As illustrated in FIG. 7, it is preferable that the plurality of microlenses 51 be disposed so as not to overlap with the lattice-shaped structural member 70 as viewed from the upper side (object side), to cause the lattice-shaped structural member 70 not to be shown in the captured image. However, due to positional deviation or the like in manufacturing, the microlenses 51 may overlap with the lattice-shaped structural member 70 as viewed from the upper side (object side) as illustrated in FIG. 10, and the lattice-shaped structural member 70 may be shown in the captured image. In such a case, it is desirable to perform image processing to cause the image of the lattice-shaped structural member 70 to be erased by the imaging processor 32. This makes it possible to increase an accuracy of the biometric authentication performed by the authentication processor 33. However, the process of the biometric authentication may also be performed on the basis of the captured image in which the image of the lattice-shaped structural member 70 remains to be shown, without performing the image processing of erasing the image of the lattice-shaped structural member 70. In this case, it is possible to increase the accuracy of the biometric authentication by performing the process of the biometric authentication using a statistical method on the captured image in which the lattice-shaped structural member 70 remains to be shown, for example. In such a case, data to be used for the process of the statistical biometric authentication may be acquired from a database or the like stored in an external server or the like.

[Illumination at Time of Imaging]

When imaging by the imaging section 20 is performed, the transparent panel section 10 may be caused to emit light to be used as illumination light for imaging. In a case where the transparent light-emitting elements 16 and the microlenses 51 are disposed as illustrated in FIG. 7 as viewed from the object side (upper side), the transparent panel section 10 causes a transparent light-emitting element 16 disposed at a position different from at least a position at which a microlens 16 to be used for the imaging is disposed, as viewed from the object side, among the plurality of transparent light-emitting elements 16 disposed in a partial region corresponding to the imaging section 20, to emit light for illumination, when the imaging by the imaging section 20 is performed.

FIG. 11 illustrates a second modification example of a relationship between a structure of the transparent panel section 10 and disposition positions of the microlenses 51 of the imaging section 20. Further, FIG. 11 illustrates an example of a light emitting state of the transparent panel section 11 at a time of imaging.

The plurality of microlenses 51 may be disposed to cause the arrangement pitch p2 of the plurality of microlenses 51 to be greater than the arrangement pitch p1 of the plurality of transparent light-emitting elements 16. In FIG. 11, the plurality of microlenses 51 is disposed to cause the arrangement pitch p2 to be twice the arrangement pitch p1 of the plurality of transparent light-emitting elements 16. However, the plurality of microlenses 51 is disposed to cause the arrangement pitch p2 to be an integral multiple of two or more of the arrangement pitch p1 of the plurality of transparent light-emitting elements 16. In this case, when the imaging is performed by the imaging section 20, the transparent panel section 10 may cause a transparent light-emitting element 16 disposed at a position different from at least a position at which a microlens 16 to be used for the imaging is disposed, as viewed from the object side, among the plurality of transparent light-emitting elements 16 disposed in the partial region corresponding to the imaging section 20, to emit light for illumination.

FIG. 12 shows a third modification example of the relation between the structure of transparent panel section 10 and disposition position of microlenses 51 of imaging section 20. FIG. 12 is a third modification example of a relationship between a configuration of the transparent panel section 10 and disposition positions of the microlenses 51 of the imaging section 20. Further, FIG. 12 illustrates an example of a light emitting state of the transparent panel section 11 at a time of imaging.

As illustrated in FIG. 12, in the transparent panel section 10, a transparent light-emitting element 17 having a segmented structure for illumination may be disposed at an outside of a region in which the plurality of microlenses 16 is disposed, as viewed from the object side. In this case, when the imaging is performed by the imaging section 20, the transparent panel section 10 may cause a transparent light-emitting element 17 having the segmented structure for illumination disposed at a position different from at least a position at which a microlens 16 to be used for the imaging is disposed among the plurality of transparent light-emitting elements 16 to emit light.

[Configuration Example of Touch Sensor]

FIG. 13 illustrates an example of a wiring structure of the transparent panel section 10. FIG. 14 illustrates an implementation example of a touch sensor function using wiring lines of the transparent panel section 10.

As illustrated in FIG. 13, the transparent panel section 10 includes, as the plurality of wiring lines for light-emitting elements, a plurality of common lines 71 to which a common drive signal is supplied and a plurality of segment lines 72 to which an individual drive signal is supplied.

The plurality of common lines 71 extends in a first direction and is arranged in a second direction that intersects the first direction. The plurality of common lines 71 is coupled to the respective plurality of transparent light-emitting elements 16 in the first direction. It is to be noted that, in FIG. 13, the first direction is a horizontal direction (a direction parallel to a left-right direction and an X direction), and the second direction is a vertical direction (a direction parallel to a top/bottom direction and a Y direction).

The plurality of segment lines 72 extends in the second direction and is arranged in the first direction. The plurality of segment lines 72 is coupled to the respective plurality of transparent light-emitting elements 16 in the second direction. One end or the other end of the plurality of segment lines 72 is pulled out so as to alternately extend to the upper right side or the lower right side in the horizontal direction.

In such a wiring structure, for example, the plurality of segment lines 72 may be divided approximately into halves of left and right portions, and a first electrode section (PAD1) may be coupled to one end side of each of the plurality of segment lines 72 included in the left half portion. In addition, a second electrode section (PAD2) may be coupled to one end side of each of the plurality of common lines 71 included in the right half potion.

Further, for example, the plurality of common lines 71 may be divided approximately into halves of top and bottom portions, and a third electrode section (PAD3) may be coupled to one end side of each of the plurality of common lines 71 included in the top half portion. In addition, a fourth electrode section (PAD4) may be coupled to one end side of each of the plurality of common lines 71 included in the bottom half portion.

Thus, as illustrated in FIG. 14, it is possible to form two sensor regions in the horizontal direction and two sensor regions in the vertical direction, a total of four sensor regions (four channels) in the top, bottom, left, and right. That is, it is possible to form: a sensor region of the first electrode section (PAD1) and the third electrode section (PAD3); a sensor region of the first electrode section (PAD1) and the fourth electrode section (PAD4); a sensor region of the second electrode section (PAD2) and the third electrode section (PAD3); and a sensor region of the second electrode section (PAD2) and the fourth electrode section (PAD4).

The common line 71 corresponds to a specific example of a "first wiring line" according to the present disclosure. The segment line 72 corresponds to a specific example of a "second wiring line" according to the present disclosure. The touch determination section 14 is able to determine a state of touch in the transparent panel section 10 on the basis of a value of capacitance between at least one wiring line out of the plurality of first wiring lines and at least one wiring line out of the plurality of second wiring lines. For example, in the example of FIG. 14, it is possible to determine the state of the touch in the top left sensor region out of the four sensor regions of top, bottom, left, and right, on the basis of a value of capacitance between the plurality of segment lines 72 corresponding to the first electrode section (PAD1) and the plurality of common lines 71 corresponding to the third electrode section (PAD3).

It is to be noted that the number into which the sensor region is to be divided is not limited to four, and may be three or less, or five or more. Further, the direction in which the sensor region is divided is not limited to two directions, and may be only one direction. For example, as illustrated in FIG. 18, which will be described later, it may have a structure such that there are four sensor regions (four channels) in the horizontal direction. Further, the case where the plurality of common lines 71 and the plurality of segment lines 72 both serve as the wiring lines for light-emitting elements and the wiring lines for touch detection has been described as an example in the above explanation; however, the plurality of common lines 71 and the plurality of segment lines 72 may be provided as the wiring lines for touch detection different from the wiring lines for the light-emitting elements. In this case, the plurality of wiring lines for light-emitting elements and the plurality of wiring lines for touch detection may be provided inside a single transparent panel section 10, or the transparent panel section 10 may have a structure in which a panel for light emission (for display) including the plurality of wiring lines for light-emitting elements and a panel for touch detection including the plurality of wiring lines for touch detection are stacked.

[1.2 Calibration of Touch Sensor]

Next, calibration of a touch sensor (the transparent panel section 10) in the electronic device 1 will be described. In a case where the transparent panel section 10 is used as a touch sensor, it is desirable to perform calibration (correction) of a determination threshold of a touch state and calibration of a working interval of the touch sensor in order to provide good sensing.

[1.2.1 Configuration Example of Control System of Electronic Device]

FIG. 15 is a configuration example of a control system of the electronic device 1 for performing calibration of the touch sensor.

The electronic device 1 includes the transparent panel section 10 serving as the touch sensor, the imaging section 20 serving as the fingerprint sensor, a CPU (Central Processing Unit) 110, a storage 113, and a communication section 114.

The CPU 110 has a function as a controller 111 and a function as a determination section 112. However, the function as the controller 111 and the function as the determination section 112 may be achieved as a program (software) to be executed by the CPU 110, or may be achieved as functions built in at least one of the transparent panel section 10 and the imaging section 20.

Further, the CPU 110 may have the functions of the touch determination section 14 and the light emission controller 15 described above (FIG. 3), and the functions of the imaging processor 32 and the authentication processor 33. The determination section 112 may include the function of the touch determination section 14.

The communication section 114 performs data communication to and from the server 115 via a wireless or wired network.

Hereinafter, a method of controlling a control parameter of touch detection will be described using the configuration of the control system illustrated in FIG. 15. The control parameter of touch detection includes, for example, a determination threshold of a touch state and a working interval of the touch sensor. Hereinafter, as examples of control parameters, methods of achieving calibration of the determination threshold of the touch state and calibration of the working interval of the touch sensor will be described.

[1.2.2 Calibration of Determination Threshold in Touch State]

First, a description will be given of a method of performing the calibration of the determination threshold of the touch state by using the function as the fingerprint sensor of the imaging section 20.

As for capacitance measured by the touch sensor, a larger value is measured as an area being in contact is larger when touched. In addition, capacitance measured by the touch sensor may vary depending on a person who performs touching or an environment. Appropriate correction (calibration) is necessary to accurately determine the touch state without such human variations or environmental variations.

FIG. 16 illustrates an outline of determination thresholds of touch states in the electronic device 1. FIG. 16 illustrates how thresholds for determining touch states are decided by combining the fingerprint sensor and the touch sensor. The upper part of FIG. 16 illustrates a relationship between capacitance (vertical axis) measured by the touch sensor and a distance (horizontal axis) between a finger 90 and a sensor surface 91 of the touch sensor. The lower part of FIG. 16 illustrates shot images of the fingerprint sensor corresponding to the distances between the finger 90 and the sensor surface 91 of the touch sensor.

As illustrated in FIG. 16, it is possible to decide the thresholds of the value of capacitance for determining a presence or absence of the touch (threshold A) and an intensity of the touch (threshold B) on the basis of the relationship between the size (area) of the fingerprint image shot by the fingerprint sensor and the value of capacitance measured by the touch sensor.

In the configuration of the control system illustrated in FIG. 15, the determination section 112 determines the state of the touch in the touch sensor on the basis of at least one determination threshold. Further, the determination section 112 determines, as the state of the touch, at least the presence or absence of the touch and the intensity of the touch.

The controller 111 has a function as a determination threshold calculation section that calculates at least one determination threshold on the basis of the value of capacitance in the touch sensor and a captured image of an object imaged by the imaging section 20 (the fingerprint image shot by the fingerprint sensor). The determination threshold calculation section calculates, as the at least one determination threshold, at least a first determination threshold (threshold A in FIG. 16) to be used for the determination of the presence or absence of the touch, and a second determination threshold (threshold B in FIG. 16) to be used for the determination of the intensity of the touch.

It is to be noted that a part or all of the functions of the controller 111 and the determination section 112 for performing calibration of the determination threshold of the touch state may be achieved as functions built in at least one of the transparent panel section 10 and the imaging section 20.

Parameter information such as the calculated determination threshold may be stored in the storage 113 or may be stored in the server 120 by the communication section 114.

FIG. 17 illustrates an outline of a process of calculating a determination threshold of a touch state in the electronic device 1.

In the electronic device 1, a value of capacitance is acquired by the touch sensor (step S101), and at the same time, a fingerprint image is shot by the fingerprint sensor (step S102).

Next, the electronic device 1 determines a pattern of the shot image (step S103). Thus, the state of the touch is estimated from an image size of the finger 90 that has been shot. For example, in a case where the electronic device 1 determines that the pattern is "no fingerprint image" in step S103, the electronic device 1 determines that the state is no touch (step S104). In a case where the electronic device 1 determines that the pattern is "fingerprint image: small" in step S103, the electronic device 1 determines that the state is a light touch (step S105). Further, in a case where the electronic device 1 determines that the pattern is "fingerprint image size: large" in step S103, the electronic device 1 determines that the state is a strong touch (step S106).

Next, the electronic device 1 determines whether data necessary for deciding the determination threshold of the touch state has been acquired (step S107). If the electronic device 1 determines that the necessary data has not been acquired (step S107: N), the electronic device 1 returns to step S101.

If the electronic device 1 determines that the necessary data has been acquired by repeating the process of acquiring the necessary data as described above (step S107: Y), the electronic device 1 then calculates the determination threshold of the touch state on the basis of the data of the relationship between the value of capacitance of the touch sensor and the state of the touch (step S108), and ends the process.

It is possible to achieve the process of deciding the determination threshold of the touch state described above, for example, by continuously and repeatedly acquiring the relationship between the distance between the finger 90 and the touch sensor and the value of capacitance of the touch sensor in a course of bringing the finger 90 close to the touch sensor when the user performs the fingerprint authentication.

[1.2.3 Calibration of Working Interval of Touch Sensor]

Here, a description will be given of a method of performing the calibration of the working interval of the touch sensor using the function as the fingerprint sensor of the imaging section 20.

In a touch sensor operation, a moving speed of the finger 90 and a time period of being in contact when performing touching are different for each user. In particular, a fast operation causes missing of data if the working interval of touch detection is long, resulting in a malfunction.

First, a description will be given of a state in which missing of data occurs. Here, it is assumed that the touch sensor has four sensor channels, ch1, ch2, ch3, and ch4.

FIG. 18 illustrates an example of an operation of the user on the touch sensor in the electronic device 1. FIG. 19 illustrates a first example of change in values of capacitance with time detected by the touch sensor in the electronic device 1. FIG. 20 illustrates a second example of change in values of capacitance with time detected by the touch sensor in the electronic device 1.

As illustrated in FIG. 18, suppose that the finger 90 is slid laterally on the touch sensor of 4 channels. FIGS. 19 and 20 each illustrate an example of change in values of capacitance with time detected by the touch sensor at this time. FIG. 19 is a graph where the working interval of the touch sensor is 8 msec, and it can be confirmed that the peaks of the values of capacitance in the respective channels sequentially appear as the finger 90 is moved.

In contrast. FIG. 20 is a graph where the working interval of the touch sensor is 30 msec. In the case where the working interval is 30 msec, the peak of the sensor channel ch3 is not confirmed. This occurs because the working interval of the touch sensor is long and a temporal resolution is low, and thereby causing missing of data when the finger 90 passes through the sensor channel ch3.

It is possible to prevent the missing of data by reducing the working interval of the touch sensor, but power consumption is increased. Therefore, it is desirable to set an optimal working interval for the operation speed so as not to cause the missing of data.

The following describes a method of, by combining the fingerprint sensor and the touch sensor, identifying a user by the fingerprint sensor and determining the optimal working interval of the touch sensor on the basis of an operation history (statistical data of the operation speeds) of the user.

In the configuration of the control system illustrated in FIG. 15, the controller 111 controls the working interval of touch detection in the touch sensor on the basis of a result of authentication performed by the authentication processor 33 (FIG. 3).

The controller 111 acquires a statistic of an operation speed of the touch of the user authenticated by the authentication processor 33 (FIG. 3), on the basis of a database related to the operation speed in which a plurality of users to be subjected to the biometric authentication by the authentication processor 33 are associated with statistics of operation speeds of touches in the touch sensor by the respective plurality of users. The controller 111 calculates a working interval of touch detection optimized for the authenticated user on the basis of the acquired statistic of the operation speed of the touch.

Parameter data for each user including the operation speed and the database related to the operation speed may be stored in the storage 113 or acquired from the server 120 by the communication section 114.

It is to be noted that a part or all of the functions of the controller 111 for performing calibration of the working interval of the touch sensor may be achieved as functions built in at least one of the transparent panel section 10 and the imaging section 20.

FIG. 21 illustrates an outline of a process of correcting a working interval of the touch sensor in the electronic device 1.

First, the electronic device 1 performs fingerprint authentication (step S201) and identifies a fingerprint pattern of a user (step S202). Next, the electronic device 1 reads out and acquires from the database a statistic related to the operation speed corresponding to the identified fingerprint pattern (steps S203, S204, and S205). It is to be noted that, although FIG. 21 illustrates an operation example in a case where the fingerprint pattern is selected from three patterns A, B, and C for the sake of explanation, the number of fingerprint patterns to be selected is not limited to three, and may be any number. Next, the electronic device 1 calculates the optimal working interval of the touch sensor for the user on the basis of the acquired statistic (step S206). Thereafter, the electronic device 1 changes the working interval of the touch sensor to the calculated value and ends the process (step S207).

FIG. 22 illustrates an example of a database of statistics related to operation speeds of users in the electronic device 1 created from operation histories of the users. FIG. 22 includes, as examples of operation speed parameters for calculating the working interval of the touch sensor, a sliding speed indicating a speed at which the finger 90 is moved laterally, and a touching speed indicating a speed at which the finger 90 is touched and released.

It is to be noted that, although FIG. 22 illustrates an example in the case where the fingerprint patterns are three patterns A. B, and C, the number of fingerprint patterns registered in the database is not limited to three, and may be any number.

[1.3 Effects]

As described above, according to the present embodiment, the imaging section 20 that images, via the transparent panel section 10, the object (the finger 90) which is in contact with or in proximity to the partial region of the transparent panel section 10 is disposed under the partial region of the transparent panel section 10; therefore, it is possible to achieve a plurality of functions in a compact size. For example, the display function and the touch sensor function may be achieved by the transparent panel section 10, and the imaging function for fingerprint authentication may be achieved by the imaging section 20.

It is to be noted that effects described in this description is merely illustrative and not limitative, and other effects may be achieved. The same applies to the following effects of other embodiments.

2. Second Embodiment

Next, an electronic device according to a second embodiment of the present disclosure will be described. It is to be noted that in the following description, the same reference numerals are given to substantially the same components as those of the electronic device according to the first embodiment, and description thereof will be omitted as appropriate.

FIGS. 23 and 24 each illustrate a main structure of an electronic device 1A according to the second embodiment of the present disclosure. FIG. 23 illustrates a structure of the transparent panel section 10 and a vicinity thereof when the electronic device 1A is viewed from the upper side (the side of an object to be imaged). FIG. 24 corresponds to a cross-section taken along a line A-A in FIG. 23.

In the first embodiment, the example (refer to FIGS. 11 and 12) has been given in which the transparent panel section 10 is partially caused to emit light to be used as the illumination light for imaging when imaging is performed by the imaging section 20; however, as illustrated in FIGS. 23 and 24, an illumination light source 80 for imaging may be separately provided.

The illumination light source 80 may be, for example, an LED (Light Emitting Diode). The illumination light source 80 is disposed at an outside of a partial region (a region corresponding to the imaging section 20) of the transparent panel section 10. The illumination light source 80 may be disposed on at least one side surface of the cover glass 3 provided on the upper side of the transparent panel section 10, for example. Thus, the light from the illumination light source 80 may be brought to the imaging section 20 by the cover glass 3. In the configuration example of each of FIGS. 23 and 24, the illumination light sources 80 are respectively disposed on two opposite sides of the cover glass 3. Thus, when imaging is performed by the imaging section 20, the illumination light may be emitted by the illumination light sources 80. Alternatively, the illumination light source 80 and the partial light emission by the transparent panel section 10 may be used in combination.

The rest of the configuration, operation, and effects may be substantially the same as those of the electronic device 1 according to the first embodiment.

3. Third Embodiment

Next, an electronic device according to a third embodiment of the present disclosure will be described. It is to be noted that in the following description, the same reference numerals are given to substantially the same components as those of the electronic device according to the first or second embodiment, and description thereof will be omitted as appropriate.

FIG. 25 illustrates a main structure of an electronic device 1B according to the third embodiment of the present disclosure. FIG. 25 illustrates a structure of the transparent panel section 10 and a vicinity thereof when the electronic device 1B is viewed from the upper side (the side of an object to be imaged).

The panel section-valid region 11 of the transparent panel section 10 is transparent as a whole; therefore, underlying structures of the panel section-valid region 11 may be visible when the transparent panel section 10 is not emitting light. For this reason, a design material 18 may be disposed under the transparent panel section 10 as illustrated in FIG. 25. The design material 18 may have a wood-grain pattern or any pattern, for example. As a result, it is possible to improve a design property.

As illustrated in FIG. 25, the design material 18 is desirably disposed under a region different from the partial region of the transparent panel section 10 (the region corresponding to the imaging section 20) as viewed from the upper side, so as not to affect the imaging of the object performed by the imaging section 20. Further, the design material 18 is desirably disposed under at least a region corresponding to the panel section-valid region 11 other than the region corresponding to the imaging section 20 as viewed from the upper side.

The rest of the configuration, operation, and effects may be substantially the same as those of the electronic device 1 according to the first embodiment.

4. Other Embodiments

Techniques according to the present disclosure are not limited to the descriptions of the above embodiments, and various modifications may be made.

For example, the present disclosure may have the following configurations.

According to the present technology having the following configuration, the imaging section that images, via the transparent panel section, the object which is in contact with or in proximity to the partial region of the transparent panel section is disposed under the partial region of the transparent panel section; therefore, it is possible to achieve a plurality of functions in a compact size. For example, the display function and the touch sensor function may be achieved by the transparent panel section, and the imaging function for fingerprint authentication may be achieved by the imaging section.

(1)

An electronic device including:

a transparent panel section in which a plurality of transparent light-emitting elements is disposed; and an imaging section that is disposed under a partial region of the transparent panel section, and images, via the transparent panel section, an object which is in contact with or in proximity to the partial region of the transparent panel section.

(2)

The electronic device according to (1), in which the imaging section includes an imaging element, and a microlens array in which a plurality of microlenses is disposed, the microlens array collecting light from the object toward the imaging element by each of the plurality of microlenses.

(3)

The electronic device according to (2), in which the imaging section further includes a light guide plate which includes a plurality of light guide paths respectively corresponding to the plurality of microlenses, the light guide plate bringing the light collected by each of the plurality of microlenses to the imaging element by each of the plurality of light guide paths.

(4)

The electronic device according to (2) or (3), in which the transparent panel section includes a lattice-shaped structural member that separates the plurality of transparent light-emitting elements from each other, and the plurality of microlenses is disposed to cause the plurality of microlenses not to overlap with the lattice-shaped structural member as viewed from side of the object.

(5)

The electronic device according to any one of (2) to (4), in which the plurality of microlenses is disposed to cause an arrangement pitch of the plurality of microlenses to be the same as an arrangement pitch of the plurality of transparent light-emitting elements, and, when imaging is performed by the imaging section, the transparent panel section causes a transparent light-emitting element to emit light, the transparent light-emitting element being included in the plurality of transparent light-emitting elements disposed in the partial region and being disposed at a position different from at least a position at which a microlens to be used for the imaging is disposed, as viewed from the side of the object.

(6)

The electronic device according to any one of (2) to (4), in which the plurality of microlenses is disposed to cause an arrangement pitch of the plurality of microlenses to be an integral multiple of two or more of an arrangement pitch of the plurality of transparent light-emitting elements.

(7)

The electronic device according to any one of (2) to (4), in which, when imaging is performed by the imaging section, the transparent panel section causes a transparent light-emitting element to emit light, the transparent light-emitting element being included in the plurality of transparent light-emitting elements, and being disposed at an outside of a region in which the plurality of microlenses is disposed and at a position different from at least a position at which a microlens to be used for the imaging is disposed among the plurality of microlenses, as viewed from the side of the object.

(8)

The electronic device according to any one of (1) to (4), further including an illumination light source that is disposed at an outside of the partial region of the transparent panel section, and emits illumination light when imaging is performed by the imaging section.

(9)

The electronic device according to any one of (1) to (8), in which the object is a portion of a living body, and the electronic device further includes an authentication processor that performs biometric authentication on the portion of the living body on a basis of a captured image of the portion of the living body obtained by imaging performed by the imaging section.

(10)

The electronic device according to (9), in which the portion of the living body is a finger, and the authentication processor performs fingerprint authentication as the biometric authentication.

(11)

The electronic device according to any one of (1) to (10), in which the transparent panel section includes, out of a plurality of wiring lines for light-emitting elements coupled to the respective plurality of transparent light-emitting elements and a plurality of wiring lines for touch detection provided separately from the plurality of wiring lines for light-emitting elements, at least the plurality of wiring lines for light-emitting elements, and has a display function to display an image using light emitted by the plurality of transparent light-emitting elements and a touch sensor function based on a value of capacitance between the plurality of wiring lines for light-emitting elements or a value of capacitance between the plurality of wiring lines for touch detection.

(12)

The electronic device according to (11), further including a determination section the determines a state of a touch in the transparent panel section, in which the transparent panel section includes, as the plurality of wiring lines for light-emitting elements or the plurality of wiring lines for touch detection, a plurality of first wiring lines that extends in a first direction, is arranged in a second direction that intersects the first direction, and is coupled to the respective plurality of transparent light-emitting elements in the first direction, and a plurality of second wiring lines that extends in the second direction, is arranged in the first direction, and is coupled to the respective plurality of transparent light-emitting elements in the second direction, and the determination section determines the state of the touch in the transparent panel section on a basis of a value of capacitance between at least one wiring line out of the plurality of first wiring lines and at least one wiring line out of the plurality of second wiring lines.

(13)

The electronic device according to (12), in which the determination section determines the state of the touch in the transparent panel section on a basis of at least one determination threshold.

(14)

The electronic device according to (13), further including a determination threshold calculation section that calculates the at least one determination threshold on a basis of the value of capacitance and a captured image of the object imaged by the imaging section.

(15)

The electronic device according to (14), in which the determination section determines, as the state of the touch, at least a presence or absence of the touch and an intensity of the touch, and the determination threshold calculation section calculates, as the at least one determination threshold, at least a first determination threshold to be used for the determination of the presence or absence of the touch, and a second determination threshold to be used for the determination of the intensity of the touch.

(16)

The electronic device according to (9) or (10), in which the transparent panel section includes, out of a plurality of wiring lines for light-emitting elements coupled to the respective plurality of transparent light-emitting elements and a plurality of wiring lines for touch detection provided separately from the plurality of wiring lines for light-emitting elements, at least the plurality of wiring lines for light-emitting elements, and has a display function to display an image using light emitted by the plurality of transparent light-emitting elements and a touch sensor function based on a value of capacitance between the plurality of wiring lines for light-emitting elements or a value of capacitance between the plurality of wiring lines for touch detection, and the electronic device further includes a controller that controls a control parameter of touch detection in the transparent panel section on a basis of a result of authentication performed by the authentication processor.

(17)

The electronic device according to (16), in which the controller acquires a statistic of an operation speed of a touch of a user authenticated by the authentication processor, on a basis of a database related to the operation speed in which a plurality of users to be subjected to the biometric authentication by the authentication processor are associated with statistics of operation speeds of touches in the transparent panel section by the respective plurality of users, and calculates, as the control parameter, a working interval of touch detection optimized for the authenticated user on a basis of the acquired statistic of the operation speed of the touch.

(18)

The electronic device according to (17), further including a storage that stores the database related to the operation speed.

(19)

The electronic device according to any one of (1) to (19), further including a design material that is disposed under a region different from the partial region of the transparent panel section.

(20)

The electronic device according to any one of (1) to (19), in which the transparent light-emitting element includes a transparent organic EL element or a quantum dot light-emitting element.

This application claims the benefit of Japanese Priority Patent Application JP2018-033776 filed with the Japan Patent Office on Feb. 27, 2018, the entire contents of which are incorporated herein by reference.

It should be understood by those skilled in the art that various modifications, combinations, sub-combinations, and alterations may occur depending on design requirements and other factors insofar as they are within the scope of the appended claims or the equivalents thereof.

The invention claimed is:

1. An electronic device comprising:
   a transparent panel in which a plurality of transparent light-emitting elements is disposed;
   an imaging sensor that is disposed under a partial region of the transparent panel, and images, via the transparent panel, an object which is in contact with or in proximity to the partial region of the transparent panel;
   an imaging element; and
   a microlens array in which a plurality of microlenses is disposed, the microlens array collecting light from the object toward the imaging element by each microlens of the plurality of microlenses, wherein
   the transparent panel includes a lattice-shaped structural member that separates the plurality of transparent light-emitting elements from each other, and
   the plurality of microlenses is disposed to cause the plurality of microlenses not to overlap with the lattice-shaped structural member as viewed from side of the object.

2. The electronic device according to claim 1, wherein the imaging sensor further includes a light guide plate which includes a plurality of light guide paths respectively corresponding to the plurality of microlenses, the light guide plate bringing the light collected by each microlens of the plurality of microlenses to the imaging element by each light guide path of the plurality of light guide paths.

3. The electronic device according to claim 1, wherein
   the plurality of microlenses is disposed to cause an arrangement pitch of the plurality of microlenses to be same as an arrangement pitch of the plurality of transparent light-emitting elements, and
   when imaging is performed by the imaging sensor, the transparent panel causes a transparent light-emitting element to emit light, the transparent light-emitting element being included in the plurality of transparent light-emitting elements disposed in the partial region and being disposed at a position different from at least a position at which a microlens to be used for the imaging is disposed, as viewed from a side of the object.

4. The electronic device according to claim 1, wherein the plurality of microlenses is disposed to cause an arrangement pitch of the plurality of microlenses to be an integral multiple of two or more of an arrangement pitch of the plurality of transparent light-emitting elements.

5. The electronic device according to claim 1, wherein, when imaging is performed by the imaging sensor, the transparent panel causes a transparent light-emitting element to emit light, the transparent light-emitting element being included in the plurality of transparent light-emitting elements, and being disposed at an outside of a region in which the plurality of microlenses is disposed and at a position different from at least a position at which a microlens to be used for the imaging is disposed among the plurality of microlenses, as viewed from a side of the object.

6. The electronic device according to claim 1, further comprising
   an illumination light source that is disposed at an outside of the partial region of the transparent panel, and emits illumination light when imaging is performed by the imaging sensor.

7. The electronic device according to claim 1, wherein
   the object is a portion of a living body, and
   the electronic device further comprises an authentication processor that performs biometric authentication on the portion of the living body on a basis of a captured image of the portion of the living body obtained by imaging performed by the imaging sensor.

8. The electronic device according to claim 7, wherein
   the portion of the living body is a finger, and
   the authentication processor performs fingerprint authentication as the biometric authentication.

9. The electronic device according to claim 1, wherein the transparent panel
   includes, out of a plurality of wiring lines for light-emitting elements coupled to respective transparent light-emitting elements of the plurality of transparent light-emitting elements and a plurality of wiring lines for touch detection provided separately from the plurality of wiring lines for light-emitting elements, at least the plurality of wiring lines for light-emitting elements, and
   has a display function to display an image using light emitted by the plurality of transparent light-emitting elements and a touch sensor function based on a value of capacitance between the plurality of wiring lines for light-emitting elements or a value of capacitance between the plurality of wiring lines for touch detection.

10. The electronic device according to claim 9, further comprising
    a determination section configured to determine a state of a touch in the transparent panel, wherein the transparent panel includes, as the plurality of wiring lines for light-emitting elements or the plurality of wiring lines for touch detection,
a plurality of first wiring lines that extends in a first direction, is arranged in a second direction that intersects the first direction, and is coupled to the respective plurality of transparent light-emitting elements in the first direction,
a plurality of second wiring lines that extends in the second direction, is arranged in the first direction, and is coupled to the respective plurality of transparent light-emitting elements in the second direction,
the determination section is further configured to determine the state of the touch in the transparent panel on a basis of a value of capacitance between at least one wiring line out of the plurality of first wiring lines and at least one wiring line out of the plurality of second wiring lines, and
the determination section is implemented via at least one processor.

11. The electronic device according to claim 10, wherein the determination section is further configured to determine the state of the touch in the transparent panel on a basis of at least one determination threshold.

12. The electronic device according to claim 11, further comprising
a determination threshold calculation section configured to calculate the at least one determination threshold on a basis of the value of capacitance and a captured image of the object imaged by the imaging sensor, wherein
the determination threshold calculation section is implemented via at least one processor.

13. The electronic device according to claim 12, wherein the determination section is further configured to determine, as the state of the touch, at least a presence or absence of the touch and an intensity of the touch, and
the determination threshold calculation section is further configured to calculate, as the at least one determination threshold, at least a first determination threshold to be used for the determination of the presence or absence of the touch, and a second determination threshold to be used for the determination of the intensity of the touch.

14. The electronic device according to claim 7, wherein the transparent panel
includes, out of a plurality of wiring lines for light-emitting elements coupled to the respective plurality of transparent light-emitting elements and a plurality of wiring lines for touch detection provided separately from the plurality of wiring lines for light-emitting elements, at least the plurality of wiring lines for light-emitting elements, and
has a display function to display an image using light emitted by the plurality of transparent light-emitting elements and a touch sensor function based on a value of capacitance between the plurality of wiring lines for light-emitting elements or a value of capacitance between the plurality of wiring lines for touch detection, and
the electronic device further comprises a controller that controls a control parameter of touch detection in the transparent panel on a basis of a result of authentication performed by the authentication processor.

15. The electronic device according to claim 14, wherein the controller acquires a statistic of an operation speed of a touch of a user authenticated by the authentication processor, on a basis of a database related to the operation speed in which a plurality of users to be subjected to the biometric authentication by the authentication processor are associated with statistics of operation speeds of touches in the transparent panel by the respective plurality of users, and calculates, as the control parameter, a working interval of touch detection optimized for the authenticated user on a basis of the acquired statistic of the operation speed of the touch.

16. The electronic device according to claim 15, further comprising
a storage that stores the database related to the operation speed.

17. The electronic device according to claim 1, further comprising
a design material that is disposed under a region different from the partial region of the transparent panel.

18. The electronic device according to claim 1, wherein the plurality of transparent light-emitting elements includes a transparent organic EL element or a quantum dot light-emitting element.

* * * * *